US007491714B2

(12) United States Patent
Axten et al.

(10) Patent No.: US 7,491,714 B2
(45) Date of Patent: Feb. 17, 2009

(54) QUINOLINES AND NITROGENATED DERIVATIVES THEREOF AND THEIR USE AS ANTIBACTERIAL AGENTS

(75) Inventors: Jeffrey Michael Axten, Collegeville, PA (US); Catherine Genevieve Yvette Dartois, Saint-Gregoire (FR); Guy Marguerite Marie Gerard Nadler, Rennes (FR); Neil David Pearson, Harlow (GB)

(73) Assignee: Glaxo Group Limited, Greenfrod, Middlesex (GB)

( * ) Notice: Subject to any disclaimer, the term of this patent is extended or adjusted under 35 U.S.C. 154(b) by 582 days.

(21) Appl. No.: 10/537,034

(22) PCT Filed: Dec. 3, 2003

(86) PCT No.: PCT/US03/38444

§ 371 (c)(1),
(2), (4) Date: Jun. 1, 2005

(87) PCT Pub. No.: WO2004/050036

PCT Pub. Date: Jun. 17, 2004

(65) Prior Publication Data
US 2006/0116512 A1 Jun. 1, 2006

Related U.S. Application Data

(60) Provisional application No. 60/469,602, filed on May 7, 2003, provisional application No. 60/430,908, filed on Dec. 4, 2002.

(51) Int. Cl.
*C07D 413/02* (2006.01)
*A61K 31/421* (2006.01)

(52) U.S. Cl. .............................. 514/211.09; 514/224.2; 514/230.5; 514/300; 514/314; 540/552; 544/48; 544/52; 544/105; 546/122; 546/177

(58) Field of Classification Search ................. 540/552; 544/48, 52, 105; 546/122, 177; 514/211.09, 514/224.2, 230.5, 300, 314
See application file for complete search history.

(56) References Cited

U.S. PATENT DOCUMENTS

| 5,861,413 | A | 1/1999 | Habich et al. | |
|---|---|---|---|---|
| 6,403,610 | B1 | 6/2002 | Malleron et al. | 514/314 |
| 6,602,882 | B1 | 8/2003 | Davies et al. | 514/300 |
| 6,603,005 | B2 | 8/2003 | Baque et al. | 546/176 |
| 6,762,200 | B2 | 7/2004 | Takagi et al. | |
| 6,903,217 | B2 | 6/2005 | Bacque et al. | 546/180 |
| 6,911,442 | B1 | 6/2005 | Davies et al. | 514/230.5 |
| 6,962,917 | B2 | 11/2005 | Davies et al. | 514/264.1 |
| 6,989,447 | B2 | 1/2006 | Markwell et al. | 546/152 |
| 7,001,913 | B1 | 2/2006 | Davies et al. | 514/300 |
| 7,141,564 | B2 | 11/2006 | Brooks et al. | 514/248 |
| 2004/0138219 | A1 | 7/2004 | Davies et al. | 514/243 |
| 2004/0224946 | A1 | 11/2004 | Bigot et al. | 514/227.8 |
| 2005/0085494 | A1 | 4/2005 | Daines et al. | 514/266.22 |
| 2005/0159411 | A1 | 7/2005 | Daines et al. | 514/224.8 |
| 2006/0014749 | A1 | 1/2006 | Davies et al. | 514/249 |
| 2006/0040925 | A1 | 2/2006 | Davies et al. | 514/222.8 |
| 2006/0040949 | A1 | 2/2006 | Surivet et al. | 514/253.04 |
| 2006/0041123 | A1 | 2/2006 | Axten et al. | 544/48 |
| 2006/0058287 | A1 | 3/2006 | Axten et al. | 514/224.2 |
| 2006/0166977 | A1 | 7/2006 | Axten et al. | 514/224.2 |
| 2006/0189601 | A1 | 8/2006 | Hennessy et al. | 514/222.8 |
| 2006/0189604 | A1 | 8/2006 | Axten et al. | 514/224.2 |
| 2006/0205719 | A1 | 9/2006 | Hubschwerlen et al. | 514/230.5 |
| 2007/0004710 | A1 | 1/2007 | Axten et al. | 514/224.2 |

FOREIGN PATENT DOCUMENTS

| EP | 0785197 A2 | 7/1997 |
|---|---|---|
| EP | 1218370 B1 | 12/2004 |
| WO | WO 99/37635 | 7/1999 |
| WO | WO 00/21948 | 4/2000 |
| WO | WO 00/21952 | 4/2000 |
| WO | WO 00/43383 | 7/2000 |
| WO | WO 00/78748 A1 | 12/2000 |
| WO | WO01/07432 A2 | 2/2001 |
| WO | WO 01/07433 A2 | 2/2001 |
| WO | WO 01/25227 A2 | 4/2001 |
| WO | WO 01/72723 | 10/2001 |
| WO | WO02/08224 A1 | 1/2002 |
| WO | WO 02/24684 A1 | 3/2002 |
| WO | WO 02/40474 A2 | 5/2002 |
| WO | WO 02/50040 A1 | 6/2002 |
| WO | WO 02/50061 A1 | 6/2002 |
| WO | WO02/056882 A1 | 7/2002 |
| WO | WO02/059116 A2 | 8/2002 |
| WO | WO03/064421 A1 | 8/2003 |

(Continued)

OTHER PUBLICATIONS

Snyder et al., PubMed Abstract (J Med Liban. 48(4):208-14) Jul.-Aug. 2000.*

(Continued)

*Primary Examiner*—Deepak Rao
(74) *Attorney, Agent, or Firm*—Loretta J. Sauermelch; Mary E. McCarthy; Charles M. Kinzig

(57) ABSTRACT

Quinoline and naphthridine derivatives useful in the treatment of bacterial infections in mammals, particularly humans.

23 Claims, No Drawings

FOREIGN PATENT DOCUMENTS

| | | |
|---|---|---|
| WO | WO03/064431 A2 | 8/2003 |
| WO | WO03/087098 A1 | 10/2003 |
| WO | WO2004/002490 A2 | 1/2004 |
| WO | WO2004/002992 A1 | 1/2004 |
| WO | WO2004/014361 A1 | 2/2004 |
| WO | WO2004/035569 A2 | 4/2004 |
| WO | WO2004/041210 A2 | 5/2004 |
| WO | WO2004/058144 A2 | 7/2004 |
| WO | WO2004/087145 A2 | 10/2004 |
| WO | WO2004/087647 | 10/2004 |
| WO | WO2004/089947 A2 | 10/2004 |
| WO | WO2004/096982 A2 | 11/2004 |

OTHER PUBLICATIONS

U.S. Appl. No. 11/604,045, filed Nov. 22, 2006, Brooks et al.

* cited by examiner

QUINOLINES AND NITROGENATED DERIVATIVES THEREOF AND THEIR USE AS ANTIBACTERIAL AGENTS

This application is a 371 of PCT/US03/38444 filed Dec. 3, 2003 which claims the benefit of U.S. Provisional Application Nos. 60/469,602 filed May 7, 2003 and 60/430,908 filed Dec. 4, 2002.

FIELD OF THE INVENTION

This invention relates to novel compounds, compositions containing them and their use as antibacterials.

BACKGROUND OF THE INVENTION

The emergence of pathogens resistant to known antibiotic therapy is becoming a serious global healthcare problem (Chu, et al., (1996) *J. Med. Chem.*, 39: 3853-3874). Thus, there is a need to discover new broad-spectrum antibiotics useful in combating multidrug-resistant organisms. Importantly, it has now been discovered that certain compounds have antibacterial activity, and therefore, may be useful for the treatment of bacterial infections in mammals, particularly in humans.

WO99/37635, WO00/21948, WO00/21952, WO00/43383, WO00/78748, WO01/07433, WO01/07432, WO01/25227, WO0208224, WO0224684, PCT/GB01/05653, PCT/GB01/05661 and WO02040474 disclose quinoline and naphthyridine derivatives having antibacterial activity.

SUMMARY OF THE INVENTION

This invention comprises compounds of the formula (I), as described hereinafter, which are useful in the treatment of bacterial infections. This invention is also a pharmaceutical composition comprising a compound according to formula (I) and a pharmaceutically acceptable carrier. This invention is also a method of treating bacterial infections in mammals, particularly in humans.

DETAILED DESCRIPTION OF THE INVENTION

This invention provides a compound of formula (I) or a pharmaceutically acceptable derivative thereof:

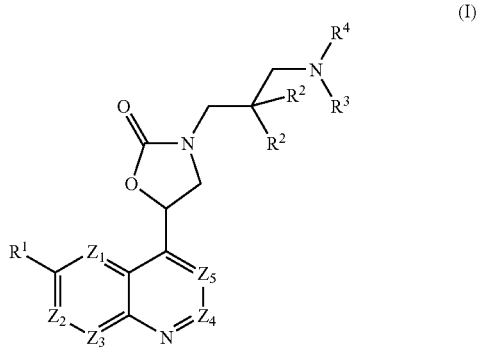

wherein:
one of $Z_1$, $Z_2$, $Z_3$, $Z_4$ and $Z_5$ is N, one is $CR^{1a}$ and the remainder are CH, or one or two of $Z_1$, $Z_2$, $Z_3$, $Z_4$ and $Z_5$ are independently $CR^{1a}$ and the remainder are CH;

$R^1$ and $R^{1a}$ are independently hydrogen; hydroxy; ($C_{1-6}$) alkoxy unsubstituted or substituted by ($C_{1-6}$)alkoxy, amino, piperidyl, guanidino or amidino any of which is optionally N-substituted by one or two ($C_{1-6}$)alkyl, acyl or ($C_{1-6}$)alkylsulphonyl groups, $CONH_2$, hydroxy, ($C_{1-6}$) alkylthio, heterocyclylthio, heterocyclyloxy, arylthio, aryloxy, acylthio, acyloxy or ($C_{1-6}$)alkylsulphonyloxy; ($C_{1-6}$) alkoxy-substituted($C_{1-6}$)alkyl; halogen; ($C_{1-6}$)alkyl; ($C_{1-6}$) alkylthio; trifluoromethyl; trifluoromethoxy; nitro; cyano; azido; acyl; acyloxy; acylthio; ($C_{1-6}$)alkylsulphonyl; ($C_{1-6}$) alkylsulphoxide; arylsulphonyl; arylsulphoxide or an amino, piperidyl, guanidino or amidino group optionally N-substituted by one or two ($C_{1-6}$)alkyl, acyl or ($C_{1-6}$) alkylsulphonyl groups; provided that when $Z_1$, $Z_2$, $Z_3$, $Z_4$ and $Z_5$ are $CR^{1a}$ or CH, then $R^1$ is not hydrogen;

each $R^2$ is independently hydrogen, OH, $NH_2$, substituted or unsubstituted ($C_{1-6}$)alkyl, or substituted or unsubstituted ($C_{1-6}$)alkoxy;

$R^3$ is H, or substituted or unsubstituted ($C_{1-6}$)alkyl;

$R^4$ is a group $-U-R^5$ where

U is selected from $CH_2$, C=O, and $SO_2$ and $R^5$ is a substituted or unsubstituted aryl group, or a substituted or unsubstituted bicyclic carbocyclic or heterocyclic ring system (A):

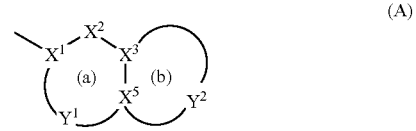

containing up to four heteroatoms in each ring in which ring (a) is aromatic and ring (b) is aromatic or non-aromatic;

$X^1$ is C;
$X^2$ is N or $CR^6$;
$X^3$ and $X^5$ are C;
$Y^1$ is a 1 to 2 atom linker group, each atom of which is independently selected from N and $CR^6$;
$Y^2$ is a 2 to 6 atom linker group, each atom of $Y^2$ being independently selected from N, $NR^8$, O, $S(O)_x$, CO, $CR^6$ and $CR^6R^7$;
each of $R^6$ and $R^7$ is independently selected from: hydrogen; ($C_{1-4}$)alkylthio; halo; carboxy($C_{1-4}$)alkyl; halo($C_{1-4}$) alkoxy; halo($C_{1-4}$)alkyl; ($C_{1-4}$)alkyl; ($C_{2-4}$)alkenyl; ($C_{1-4}$) alkoxycarbonyl; formyl; ($C_{1-4}$)alkylcarbonyl; ($C_{2-4}$)alkenyloxycarbonyl; ($C_{2-4}$)alkenylcarbonyl; ($C_{1-4}$) alkylcarbonyloxy; ($C_{1-4}$)alkoxycarbonyl($C_{1-4}$)alkyl; hydroxy; hydroxy($C_{1-4}$)alkyl; mercapto($C_{1-4}$)alkyl; ($C_{1-4}$) alkoxy; nitro; cyano; carboxy; amino or wherein the amino group is optionally substituted by ($C_{1-4}$)alkoxycarbonyl, ($C_{1-4}$)alkylcarbonyl, ($C_{2-4}$)alkenyloxycarbonyl, ($C_{2-4}$)alkenylcarbonyl, ($C_{1-4}$)alkyl or ($C_{2-4}$)alkenyl and optionally further substituted by ($C_{1-4}$)alkyl or ($C_{2-4}$)alkenyl; or ($C_{2-6}$) alkenyl; ($C_{1-4}$)alkylsulphonyl; ($C_{2-4}$)alkenylsulphonyl; or aminosulphonyl wherein the amino group is optionally mono- or di-substituted by ($C_{1-4}$)alkyl or ($C_{2-4}$)alkenyl; aryl; aryl($C_{1-4}$)alkyl; aryl($C_{1-4}$)alkoxy;

each $R^8$ is independently hydrogen; trifluoromethyl; ($C_{1-4}$) alkyl unsubstituted or substituted by hydroxy, ($C_{1-6}$) alkoxy, ($C_{1-6}$)alkylthio, halo or trifluoromethyl; ($C_{2-4}$)alkenyl; aryl; aryl ($C_{1-4}$)alkyl; arylcarbonyl; heteroarylcarbonyl; ($C_{1-4}$)alkoxycarbonyl; ($C_{1-4}$)alkylcarbonyl; formyl; ($C_{1-6}$)alkylsulphonyl; or aminocarbonyl wherein the amino group is optionally substituted by $(C_{1-4})$ alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$alkyl or $(C_{2-4})$alkenyl; and x is 0, 1, or 2;

Also included in this invention are pharmaceutically acceptable addition salts, complexes or prodrugs of the compounds of this invention. Prodrugs are considered to be any covalently bonded carriers which release the active parent drug according to formula (I) in vivo.

The invention also provides a pharmaceutical composition, in particular for use in the treatment of bacterial infections in mammals, particularly humans, comprising a compound of formula (I), or a pharmaceutically acceptable derivative thereof, and a pharmaceutically acceptable carrier.

The invention further provides a method of treatment of bacterial infections in mammals, particularly in humans, which method comprises the administration to a mammal in need of such treatment an effective amount of a compound of formula (I), or a pharmaceutically acceptable derivative thereof.

Preferably $Z_5$ is CH or N, $Z_3$ is CH or CF and $Z_1$, $Z_2$ and $Z_4$ are each CH, or $Z_1$ is N, $Z_3$ is CH or CF and $Z_2$, $Z_4$ and $Z_5$ are each CH.

When $R^1$ or $R^{1a}$ is substituted alkoxy it is preferably $(C_{2-6})$ alkoxy substituted by optionally N-substituted amino, guanidino or amidino, or $(C_{1-6})$alkoxy substituted by piperidyl. Suitable examples of $R^1$ and $R^{1a}$ alkoxy include methoxy, trifluoromethoxy, n-propyloxy, iso-butyloxy, aminoethyloxy, aminopropyloxy, aminobutyloxy, aminopentyloxy, guanidinopropyloxy, piperidin-4-ylmethyloxy, phthalimido pentyloxy or 2-aminocarbonylprop-2-oxy.

Preferably $R^1$ and $R^{1a}$ are independently methoxy, amino $(C_{3-5})$alkyloxy, guanidino$(C_{3-5})$alkyloxy, piperidyl$(C_{3-5})$ alkyloxy, nitro or halo; more preferably methoxy, amino $(C_{3-5})$ alkyloxy or guanidino$(C_{3-5})$alkyloxy. Most preferably $R^1$ is methoxy and $R^{1a}$ is H or when $Z_3$ is $CR^{1a}$ it may be C—F. Preferably $R^5$ is substituted or unsubstituted aryl, most preferably substituted or unsubstituted phenyl.

When $Z_5$ is $CR^{1a}$, $R^{1a}$ is preferably hydrogen, cyano, hydroxymethyl or carboxy, most preferably hydrogen.

Preferably in the heterocyclic ring (A) $Y^2$ has 3-5 atoms, more preferably 4 atoms including $NR^8$, O or S bonded to $X^5$ and NHCO bonded via N to $X^3$, or O or NH bonded to $X^3$. Ring (a) is preferably substituted and unsubstituted phenyl, pyridine, pyrrole, and imidazole. Preferably ring (b) is substituted and unsubstituted phenyl, pyridine, dioxane, piperidine, morpholin-3-one, thiomorpholin-3-one, oxazolidin-2-one, thiadiazole, and thiazepan-5-one.

Preferably $R^6$ and $R^7$ are independently hydrogen; halo; carboxy$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$ alkoxycarbonyl$(C_{1-4})$alkyl; hydroxy; hydroxy$(C_{1-4})$ alkyl; $(C_{1-4})$alkoxy; nitro; cyano; carboxy; amino or wherein the amino group is optionally substituted by $(C_{1-4})$alkyl or $(C_{2-4})$alkenyl and optionally further substituted by $(C_{1-4})$ alkyl or $(C_{2-4})$alkenyl; or $(C_{2-6})$alkenyl;

Most preferably $R^6$ and $R^7$ are hydrogen, hydroxy, halo, or $(C_{1-4})$alkyl substituted or unsubstituted by hydroxy, $(C_{1-6})$ alkoxy, $(C_{1-6})$alkylthio, halo or trifluoromethyl; $(C_{2-4})$alkenyl; $(C_{1-4})$alkoxycarbonyl.

Preferably $R^8$ is hydrogen; trifluoromethyl; $(C_{1-4})$alkyl unsubstituted or substituted by hydroxy, $(C_{1-6})$alkoxy, $(C_{1-6})$ alkylthio, halo or trifluoromethyl; $(C_{2-4})$alkenyl; $(C_{1-4})$ alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkyl or $(C_{2-4})$alkenyl and optionally further substituted by $(C_{1-4})$alkyl or $(C_{2-4})$alkenyl.

Most preferably $R^8$ is $C_{1-4}$)alkyl or $(C_{2-4})$alkenyl and optionally further substituted by $(C_{1-4})$alkyl or $(C_{2-4})$alkenyl.

Examples of $R^5$ groups include substituted and unsubstituted:

1,1,3-trioxo-1,2,3,4-tetrahydro1 β-benzo[1,4] thiazin-3-one-6-yl, benzo[1,3]dioxol-5-yl, 4H-benzo[1,4]oxazin-3-one-6-yl, 2,3-dihydro-benzo[1,4]dioxin-6-yl, 2-oxo-2,3-dihydro-benzooxazol-6-yl, 3-substituted-3H-benzooxazol-2-one-6-yl, 3-substituted-3H-benzooxazole-2-thione-6-yl, 3-substituted-3H-benzothiazol-2-one-6-yl, 4H-benzo[1,4] oxazin-3-one-6-yl (3-oxo-3,4-dihydro-2H-benzo[1,4]oxazin-6-yl), 4H-benzo[1,4]thiazin-3-one-6-yl (3-oxo-3,4-dihydro-2H-benzo[1,4]thiazin-6-yl), 4H-benzo[1,4] oxazin-3-one-7-yl, 4-oxo-2,3,4,5-tetrahydro-benzo[b][1, 4]thiazepine-7-yl, 5-oxo-2,3-dihydro-5H-thiazolo[3,2-a] pyrimidin-6-yl, benzo[1,3]dioxol-5-yl, 1H-pyrido[2,3 b][1,4]thiazin-2-one-7-yl (2-oxo-2,3-dihydro-1H-pyrido [2,3-b]thiazin-7-yl), 2,3-dihydro-1H-pyrido[2,3-b][1,4] thiazin-7-yl, 2-oxo-2,3-dihydro-1H-pyrido[3,4-b]thiazin-7-yl, 2,3-dihydro-[1,4]dioxino[2,3-b]pyridin-6-yl, 2,3-dihydro-[1,4]dioxino[2,3-c]pyridin-7-yl, 2,3-dihydro-[1,4]dioxino[2,3-b]pyridin-7-yl, 3,4-dihydro-2H-benzo[1,4] oxazin-6-yl, 3,4-dihydro-2H-benzo[1,4]thiazin-6-yl, 3-oxo-3,4-dihydro-2H-pyrido[3,2-b][1,4]oxazin-6-yl, 3,4-dihydro-2H-pyrido[3,2-b][1,4]thiazin-6-yl, 3-oxo-3,4-dihydro-2H-pyrido[3,2-b][1,4]thiazin-6-yl, 3,4-dihydro-1H-quinolin-2-one-7-yl, 3,4-dihydro-1H-quinoxalin-2-one-7-yl, 6,7-dihydro-4H-pyrazolo[1,5-a]pyrimidin-5-one-2-yl, 5,6,7,8-tetrahydro-[1,8]naphthyridin-2-yl, 2-oxo-3,4-dihydro-1H[1,8]naphthyridin-6-yl, 1H-Indol-2-yl, 2-(3,5-Difluoro-phenoxy)-methyl-2yl, quinolin-8-ol-2-yl, 3-Oxo-3,4-dihydro-2H-benzo[1,4]oxazine-6-yl, 4H-benzo[1,4]oxazin-3-one-6-yl, 4-Fluoro-1H-benzoimidazol-2-yl, 3,6-dimethyl-3H-benzooxazol-2-one, 4H-benzo[1,4]thiazin-3-one-6-yl, 3-Oxo-3,4-dihydro-2H-benzo[1,4]thiazine-6-yl, 4-Oxo-2,3,4,5-tetrahydro-benzo [b][1,4]thiazepine-7-yl, 7-Chloro-3-oxo-3,4-dihydro-2H-benzo[1,4]thiazine-6-yl, 3-oxo-3,4-dihydro-2H-pyrido[3, 2-b][1,4]oxazine-6-yl, and 4H-pyrido[3,2-b][1,4]oxazin-3-one-yl.

Preferred $R^5$ groups include 1H-Indol-2-yl, quinolin-8-ol-2-yl, 3-Oxo-3,4-dihydro-2H-benzo[1,4]oxazine-6-yl, 4H-benzo[1,4]oxazin-3-one-6-yl, 4-Fluoro-1H-benzoimidazol-2-yl, 3,6-dimethyl-3H-benzooxazol-2-one, 4H-benzo[1, 4]thiazin-3-one-6-yl, 3-Oxo-3,4-dihydro-2H-benzo[1,4]thiazine-6-yl, 4-Oxo-2,3,4,5-tetrahydro-benzo[b][1,4] thiazepine-7-yl, 7-Chloro-3-oxo-3,4-dihydro-2H-benzo[1,4] thiazine-6-yl, 3-oxo-3,4-dihydro-2H-pyrido[3,2-b][1,4] oxazine-6-yl, and 4H-pyrido[3,2-b][1,4]oxazin-3-one-yl.

Preferred compounds of this invention are:

3-Oxo-3,4-dihydro-2H-benzo[1,4]thiazine-6-sulfonic acid {3-[(R)-5-(6-methoxy-quinolin-4-yl)-2-oxo-oxazolidin-3-yl]-propyl}-amide;

4-Oxo-2,3,4,5-tetrahydro-benzo[b][1,4]thiazepine-7-sulfonic acid {3-[(R)-5-(6-methoxy-quinolin-4-yl)-2-oxo-oxazolidin-3-yl]-propyl}-amide;

3-Oxo-3,4-dihydro-2H-benzo[1,4]oxazine-6-sulfonic acid {3-[(R)-5-(6-methoxy-quinolin-4-yl)-2-oxo-oxazolidin-3-yl]-propyl}-amide;

7-Chloro-3-oxo-3,4-dihydro-2H-benzo[1,4]thiazine-6-sulfonic acid {3-[(R)-5-(6-methoxy-quinolin-4-yl)-2-oxo-oxazolidin-3-yl]-propyl}-amide;

3-Oxo-3,4-dihydro-2H-benzo[1,4]thiazine-6-sulfonic acid {3-[(R)-5-(8-fluoro-6-methoxy-quinolin-4-yl)-2-oxo-oxazolidin-3-yl]-propyl}-amide;

3-Oxo-3,4-dihydro-2H-benzo[1,4]thiazine-6-sulfonic acid {3-[(R)-5-(6-methoxy-[1,5]naphthyridin-4-yl)-2-oxo-oxazolidin-3-yl]-propyl}-amide;

3-Oxo-3,4-dihydro-2H-benzo[1,4]thiazine-6-sulfonic acid {3-[(S)-5-(6-methoxy-[1,5]naphthyridin-4-yl)-2-oxo-oxazolidin-3-yl]-propyl}-amide;

3-Oxo-3,4-dihydro-2H-benzo[1,4]oxazine-6-sulfonic acid {3-[(R)-5-(6-methoxy-[1,5]naphthyridin-4-yl)-2-oxo-oxazolidin-3-yl]-propyl}-amide;

3-Oxo-3,4-dihydro-2H-pyrido[3,2-b][1,4]thiazine-6-carboxylic acid {3-[(R)-5-(6-methoxy-quinolin-4-yl)-2-oxo-oxazolidin-3-yl]-propyl}-amide;

(R)-3-{3-[(1H-Indol-2-ylmethyl)-methyl-amino]-propyl}-5-(6-methoxy-quinolin-4-yl)-oxazolidin-2-one;

(R)-3-{3-[(Benzo[1,2,5]thiadiazole-5-ylmethyl)-amino]-propyl}-5-(6-methoxy-quinolin-4-yl)-oxazolidin-2-one;

(R)-3-{3-[(1H-Indol-2-ylmethyl)-amino]-propyl}-5-(6-methoxy-quinolin-4-yl)-oxazolidin-2-one;

(R)-3-{3-[(8-Hydroxy-quinolin-2-ylmethyl)-methyl-amino]-propyl}-5-(6-methoxy-quinolin-4-yl)-oxazolidin-2-one;

(R)-3-{3-[(4-Fluoro-1H-benzoimidazol-2-ylmethyl)-amino]-propyl}-5-(6-methoxy-quinolin-4-yl)-oxazolidin-2-one;

6-({3-[(R)-5-(6-Methoxy-quinolin-4-yl)-2-oxo-oxazolidin-3-yl]-propylamino}-methyl-4H-benzo[1,4]oxazin-3-one;

(R)-3-{3-[(8-Hydroxy-quinolin-2-ylmethyl)-amino]-propyl}-5-(6-methoxy-quinolin-4-yl)-oxazolidin-2-one;

(6-({3-[(R)-5-(6-Methoxy-quinolin-4-yl)-2-oxo-oxazolidin-3-yl]-propylamino}-methyl-4H-benzo[1,4]thiazin-3-one;

6-({3-[(R)-5-(6-Methoxy-quinolin-4-yl)-2-oxo-oxazolidin-3-yl]-propylamino}-methyl)-4H-pyrido[3,2-b][1,4]oxazin-3-one;

6-({3-[(R)-5-(8-Fluoro-6-methoxy-quinolin-4-yl)-2-oxo-oxazolidin-3-yl]-propylamino}-methyl)-4H-pyrido[3,2-b][1,4]oxazin-3-one;

3-Oxo-3,4-dihydro-2H-benzo[1,4]thiazine-6-sulfonic acid{3-[(R)-5-(6-methoxy-[1,5]naphthyridin-4-yl)-2-oxo-oxazolidin-3-yl ]-2,2-dimethyl-propyl}-amide;

2,3-Dihydro-benzo[1,4]dioxine-6-sulfonic acid {3-[5-(6-methoxy-[1,5]naphthyridin-4-yl)-2-oxo-oxazolidin-3-yl]-propyl}-amide;

6-({3-[5-(6-Methoxy-[1,5]naphthyridin-4-yl)-2-oxo-oxazolidin-3-yl]-propylamino}-methyl)-41+pyrido[3,2-b][1,4]thiazin-3-one;

6-({3-[5-(6-Methoxy-[1,5]naphthyridin-4-yl)-2-oxo-oxazolidin-3-yl]-propylamino}-methyl)-4H-pyrido[3,2-b][1,4]oxazin-3-one;

3-Oxo-3,4-dihydro-2H-benzo[1,4]thiazine-6-sulfonic acid {(R)-2-hydroxy-3-[(R)-5-(6-methoxy-[1,5]naphthyridin-4-yl)-2-oxo-oxazolidin-3-yl]-propyl}-amide;

6-({(S)-2-Hydroxy-3-[(R)-5-(6-methoxy-[1,5]naphthyridin-4-yl)-2-oxo-oxazolidin-3-yl]-propylamino}-methyl)-4H-pyrido[3,2-b][1,4]thiazin-3-one;

3-Oxo-3,4-dihydro-2H-benzo[1,4]thiazine-6-sulfonic acid {(S)-2-hydroxy-3-[(R)-5-(6-methoxy-[1,5]naphthyridin-4-yl)-2-oxo-oxazolidin-3-yl]-propyl}-amide; and 6-({(R)-2-Hydroxy-3-[(R)-5-(6-methoxy-[1,5]naphthyridin-4-yl)-2-oxo-oxazolidin-3-yl]-propylamino}-methyl)-4H-pyrido[3,2-b][1,4]thiazin-3-one; or a pharmaceutically acceptable salt thereof.

Unless otherwise defined, the term $(C_{1-6})$alkyl when used alone or when forming part of other groups (such as the 'alkoxy' group) includes substituted or unsubstituted, straight or branched chain alkyl groups containing 1 to 6 carbon atoms. Examples of $(C_{1-6})$alkyl include methyl, ethyl, n-propyl, isopropyl, n-butyl, isobutyl and tert-butyl groups.

The term $(C_{2-6})$alkenyl means a substituted or unsubstituted alkyl group of 2 to 6 carbon atoms, wherein one carbon-carbon single bond is replaced by a carbon-carbon double bond. Examples of $(C_{2-6})$alkenyl include ethylene, 1-propene, 2-propene, 1-butene, 2-butene, isobutene and the several isomeric pentenes and hexenes. Both cis and trans isomers are included.

The term $(C_{3-7})$cycloalkyl refers to subsituted or unsubstituted carbocyclic system of three to seven carbon atoms, which may contain up to two unsaturated carbon-carbon bonds. Examples of $(C_{3-7})$cycloalkyl include cyclopropyl, cyclobutyl, cyclopentyl, cyclopentenyl, cyclohexyl, cyclohexenyl, and cycloheptyl.

Unless otherwise defined, suitable substituents for any $(C_{1-6})$alkyl, $(C_{2-6})$alkenyl, $(C_{1-6})$alkoxy and $(C_{3-7})$cycloalkyl groups includes up to three substituents selected from the group consisting of hydroxy, halogen, nitro, cyano, carboxy, amino, amidino, sulphonamido, unsubstituted $(C_{1-6})$alkyl, unsubstituted $(C_{1-6})$alkoxy, trifluromethyl, acyloxy, quanidino, unsubstituted $(C_{3-7})$cycloalkyl, aryl, and heterocyclic.

Halo or halogen includes fluoro, chloro, bromo and iodo.

Haloalkyl moieties include 1-3 halogen atoms.

Unless otherwise defined, the term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or C-substituted by, for example, up to three groups selected from $(C_{1-4})$ alkylthio; halo; carboxy$(C_{1-4})$alkyl; halo $(C_{1-4})$alkoxy; halo $(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$ alkoxycarbonyl$(C_{1-4})$alkyl; hydroxy; hydroxy $(C_{1-4})$alkyl; mercapto$(C_{1-4})$alkyl; $(C_{1-4})$alkoxy; nitro; cyano, carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; optionally substituted aryl, aryl$(C_{1-4})$alkyl or aryl$(C_{1-4})$ alkoxy and oxo groups.

Each heterocyclic ring suitably has from 4 to 7, preferably 5 or 6, ring atoms. A fused heterocyclic ring system may include carbocyclic rings and need include only one heterocyclic ring.

Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include H; trifluoromethyl; $(C_{1-4})$alkyl optionally substituted by hydroxy, $(C_{1-6})$alkoxy, $(C_{1-6})$alkylthio, halo or trifluoromethyl; $(C_{2-4})$alkenyl; aryl; aryl $(C_{1-4})$alkyl; $(C_{1-4})$alkoxycarbonyl; $(C_{1-4})$alkylcarbonyl; formyl; $(C_{1-6})$alkylsulphonyl; or aminocarbonyl wherein the amino group is optionally substituted by $(C_{1-4})$alkoxycarbonyl, $(C_{1-4})$alkylcarbonyl, $(C_{2-4})$ alkenyloxycarbonyl, $(C_{2-4})$alkenylcarbonyl, $(C_{1-4})$alkyl or $(C_{2-4})$alkenyl and optionally further substituted by $(C_{1-4})$ alkyl or $(C_{2-4})$alkenyl.

When used herein the term "aryl", includes optionally substituted phenyl and naphthyl.

Aryl groups may be optionally substituted with up to five, preferably up to three, groups selected from $(C_{1-4})$alkylthio; halo; carboxy$(C_{1-4})$alkyl; halo $(C_{1-4})$alkoxy; halo$(C_{1-4})$alkyl; $(C_{1-4})$alkyl; $(C_{2-4})$alkenyl; $(C_{1-4})$alkoxycarbonyl; formyl; $(C_{1-4})$alkylcarbonyl; $(C_{2-4})$alkenyloxycarbonyl; $(C_{2-4})$alkenylcarbonyl; $(C_{1-4})$alkylcarbonyloxy; $(C_{1-4})$alkoxycarbonyl $(C_{1-4})$alkyl; hydroxy; hydroxy $(C_{1-4})$alkyl; mercapto$(C_{1-4})$alkyl; $(C_{1-4})$alkoxy; nitro; cyano; carboxy; amino or aminocarbonyl optionally substituted as for corresponding substituents in $R^3$; $(C_{1-4})$alkylsulphonyl; $(C_{2-4})$alkenylsulphonyl; or aminosulphonyl wherein the amino group is optionally substituted by $(C_{1-4})$alkyl or $(C_{2-4})$alkenyl; phenyl, phenyl$(C_{1-4})$alkyl or phenyl$(C_{1-4})$alkoxy The term "acyl" includes formyl and $(C_{1-6})$alkylcarbonyl group.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Pharmaceutically acceptable derivatives of the above-mentioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming esters which break down readily in the human body to leave the parent acid or its salt. Suitable groups of this type include those of part formulae (i), (ii), (iii), (iv) and (v):

$$-\overset{R^a}{\underset{|}{CH}}-O\cdot CO\cdot R^b \quad (i)$$

$$-R^c-N\overset{R^d}{\underset{R^e}{\diagup}} \quad (ii)$$

$$-CH_2-OR^f \quad (iii)$$

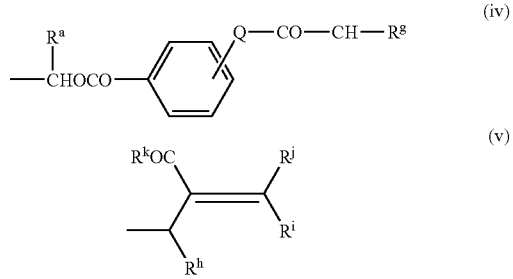

(iv)

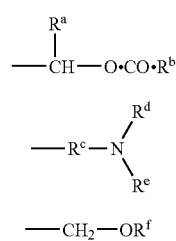

(v)

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$ alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene; $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino $(C_{1-4})$alkyl groups such as dimethylaminomethyl, dimethylaminoethyl, diethylaminomethyl or diethylaminoethyl; 2-(($C_{1-6}$)alkoxycarbonyl)-2-($C_{2-6}$)alkenyl groups such as 2-(isobutoxycarbonyl)pent-2-enyl and 2-(ethoxycarbonyl) but-2-enyl; lactone groups such as phthalidyl and dimethoxyphthalidyl.

A further suitable pharmaceutically acceptable in vivo hydrolysable ester-forming group is that of the formula:

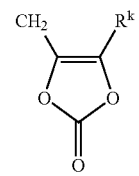

wherein $R^k$ is hydrogen, $C_{1-6}$ alkyl or phenyl.

R is preferably hydrogen.

Certain of the above-mentioned compounds of formula (I) may exist in the form of optical isomers, e.g. diastereoisomers and mixtures of isomers in all ratios, e.g. racemic mixtures.

The invention includes all such forms, in particular the pure isomeric forms. For examples the invention includes compound in which an A-B group CH(OH)—CH$_2$ is in either isomeric configuration the R-isomer is preferred. The different isomeric forms may be separated or resolved one from the other by conventional methods, or any given isomer may be obtained by conventional synthetic methods or by stereospecific or asymmetric syntheses.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DEAD refers to diethyl azodicarboxylate, PPh$_3$ refers to triphenylphosphine, DIAD refers to diisopropyl azodicarboxylate, DME refers to dimethoxyethane, DMF refers to dimethylformamide, NBS refers to N-bromosuccinimide, Pd/C refers to a palladium on carbon catalyst, PPA refers to polyphosphoric acid, DPPA refers to diphenylphosphoryl azide, BOP refers to benzotriazol-1-yloxy-tris(dimethylamino)phosphonium hexafluorophosphate, HF refers to hydrofluoric acid, TEA refers to triethylamine, TFA refers to trifluoroacetic acid, PCC refers to pyridinium chlorochromate.

The oxazolidinone compounds were prepare as shown in Scheme I.

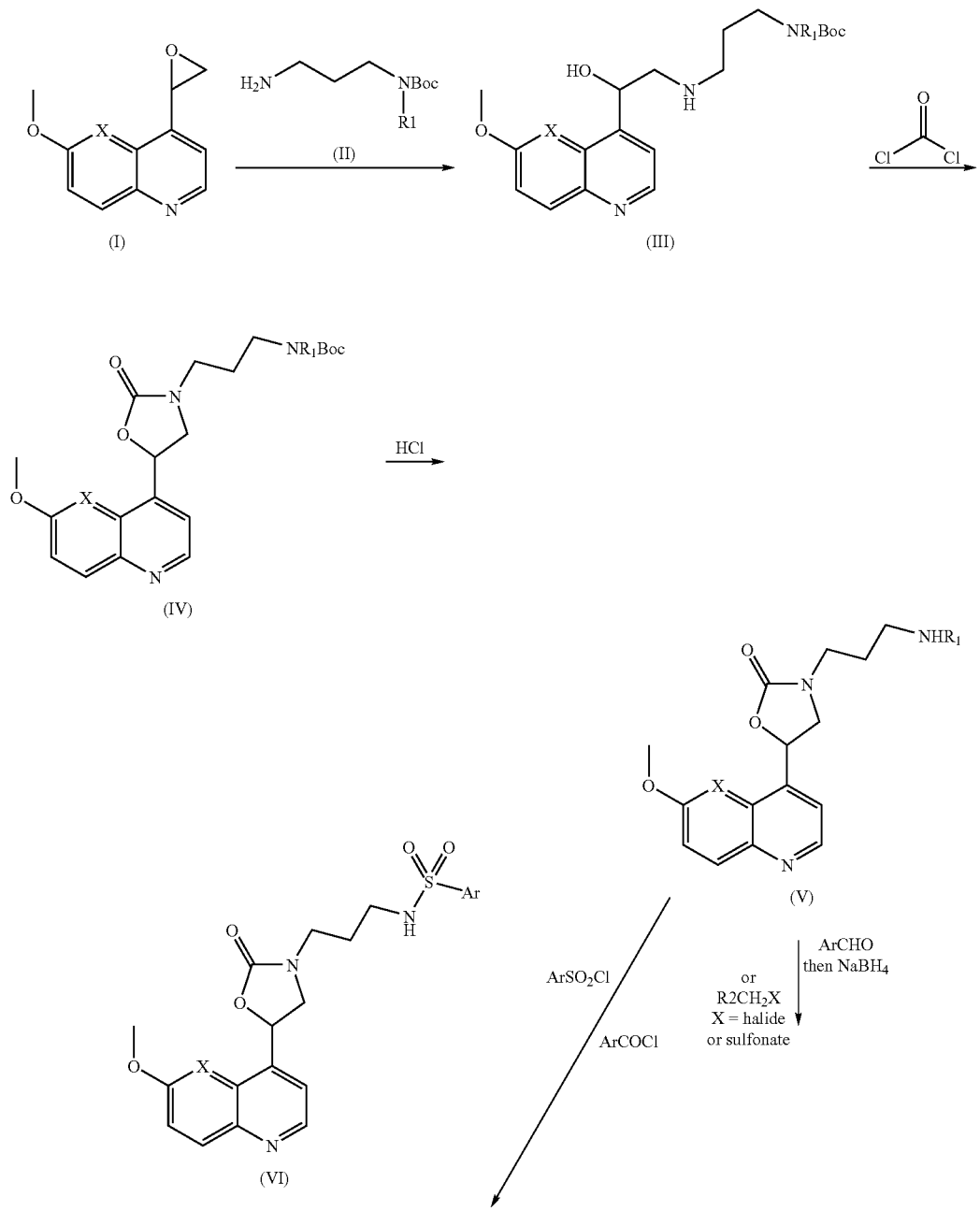

-continued

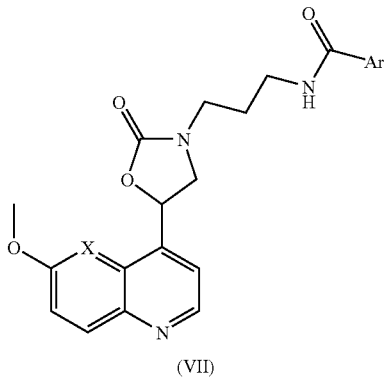

(VII)

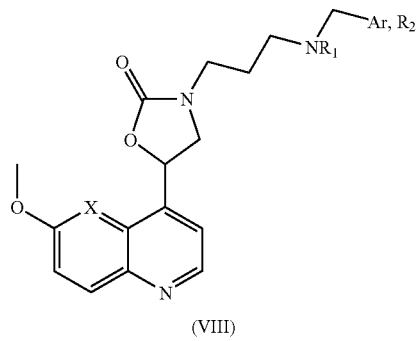

(VIII)

Enantiomerically enriched epoxides of type (I) can be prepared prepared from 6-methoxyquinoline-4-carboxylic acid as described in the example. Compounds of type (I) wherein X=N can be prepared in enantiomerically enriched form starting with 3-amino-6-methoxypyridine as described in the example. The aryl epoxide (I) (>92% ee), and a monoprotected 1,3-diaminopropane (II) were heated in DMF to provide the aminoalcohols (III). Treatment with triphosgene (or a similar phosgene substitute (e.g, 1,1'-carbonyldiimidazole) in the presence of a weak base such as triethylamine affords oxazolidinones (IV), which are then deprotected with HCl in dioxane. Alternatively, a mixture of trifluoroacetic acid in an organic solvent may be used. The resulting amines (V) can be reacted with a tertiary amine base and appropriate sulfonyl chloride to give the sulfonamides (VI) by standard methods. Alternatively, an acid chloride is used in place of the sulfonyl chloride to prepare the corresponding amides (VII). A reductive amination procedure applied to the amine (V) afforded secondary amines (VIII). The reductive amination can be carried out by well established methods. This includes complete formation of imine prior to reduction with a hydride source, and single pot procedures which reduce the imine as it is formed. Additionally, the amines (V) can be alkylated with an alkyl halide, mesylate or tosylate by standard methods to give the amine products (VIII).

The pharmaceutical compositions of the invention include those in a form adapted for oral, topical or parenteral use and may be used for the treatment of bacterial infection in mammals including humans.

The antibiotic compounds according to the invention may be formulated for administration in any convenient way for use in human or veterinary medicine, by analogy with other antibiotics.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the compositions comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable salt or in vivo hydrolysable ester thereof is administered in the above-mentioned dosage range.

The compound of formula (I) may be the sole therapeutic agent in the compositions of the invention or a combination with other antibiotics or with a β-lactamase inhibitor may be employed.

Compounds of formula (I) are active against a wide range of organisms including both Gram-negative and Gram-positive organisms.

Biological Activity

Antimicrobial Activity Assay:

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically". The compounds were tested in serial two-fold dilutions ranging from 0.016 to 64 mcg/mL. Compounds were evaluated against a panel of Gram-(+) organisms, including *Staphylococcus aureus* WCUH29, *Staphylococcus epidermidis* CL7, *Streptococcus pneumoniae* 1629, *Streptococcus pyogenes* CN 10, *Enterococcus faecalis* 2, and *Enterococcus faecium* 8. In addition, compounds were evaluated against a panel of Gram-(−) strains including *Haemophilus influenzae* NEMC1, *E. coli* 7623 AcrABEFD+, and *Moraxella catarrhalis* Ravasio. The minimum inhibitory concentration (MIC) was determined as the lowest concentration of compound that inhibited visible growth. A mirror reader was used to assist in determining the MIC endpoint.

One skilled in the art would consider any compound with a MIC of less than 64 µg/mL to be a potential lead compound. Preferably, the compounds used in the antimicrobial assays of the present invention have a MIC value of less than 16 µg/mL.

The following examples illustrate the preparation of certain compounds of formula (I).

Experimental

General

Proton nuclear magnetic resonance ($^1$H NMR) spectra were recorded at 300 MHz, and chemical shifts are reported in parts per million (δ) downfield from the internal standard tetramethylsilane (TMS). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. CDCl$_3$ is deuteriochloroform, DMSO-d$_6$ is hexadeuteriodimethylsulfoxide, and CD$_3$OD is tetradeuteriomethanol. Mass spectra were obtained using electrospray (ES) ionization techniques. Elemental analyses were performed by Quantitative Technologies Inc., White-house, N.J. Melting points were obtained on a Thomas-Hoover melting point apparatus and are uncorrected. All temperatures are reported in degrees Celsius. E. Merck Silica Gel 60 F-254 thin layer plates were used for thin layer chromatography. Flash chromatography was carried out on E. Merck Kieselgel 60 (230-400 mesh) silica gel. Analytical HPLC was performed on Beckman chromatography systems. Preparative HPLC was performed using Gilson chromatography systems. ODS refers to an octadecylsilyl derivatized silica gel chromatographic support. YMC ODS-AQ® is an ODS chromatographic support and is a registered trademark of YMC Co. Ltd., Kyoto, Japan. PRP-1® is a polymeric (styrene-divinylbenzene) chromatographic support, and is a registered trademark of Hamilton Co., Reno, Nev. Celite® is a filter aid composed of acid-washed diatomaceous silica, and is a registered trademark of Manville Corp., Denver, Colo.

EXAMPLES

Example 1

3-Oxo-3,4-dihydro-2H-benzo[1,4]thiazine-6-sulfonic acid {3-[(R)-5-(6-methoxy-quinolin-yl)-2-oxo-oxazolidin-3-yl]-propyl}-amide A solution of 6-methoxyquinoline-4-carboxylic acid (10 g) in dichloromethane was heated under reflux with oxalyl chloride (5 ml) and dimethylformamide (2 drops) for 1 hour and evaporated to dryness. The residue, in dichloromethane (100 ml) was treated with a 2M solution of trimethylsilyldiazomethane in hexane (50 ml) and stirred at room temperature for 18 hours. 5M Hydrochloric acid (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). A batch of the chloromethyl ketone (20 g) was reduced with (+)-B-chlorodiisopinocamphenylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuran (100 ml) and reacted with sodium hydroxide (2.6 g) in water (13 ml) for 1.5 hours. The reaction mixture was evaporated to dryness and chromatographed on silica gel eluting with ethyl acetate-hexane to give 6-Methoxy-4-(R)-oxiranyl-quinoline as a solid (10.4 g) (84% ee by chiral HPLC). Recrystallisation from ether-pentane gave mother-liquor (7.0 g) (90% ee).

MS (ES) m/e 202 (M+H$^+$).

The absolute stereochemistry was defined to be (R) by an NMR study on the Mosher's esters derived from the product obtained by reaction with 1-t-butylpiperazine.

A solution of the above epoxide (690 mg, 3.43 mmole) and (3-amino-propyl)-carbamic acid tert-butyl ester (Aldrich, 600 mg, 3.43 mmole) in DMF (5 mL) was heated in a 60° C. oil bath for 8 hours. The mixture was evaporated ot dryness and the product purified by chromatography on silica using 90:10:1 CHCl$_3$:MeOH: aq. NH$_4$OH to afford a pale yellow thick oil (550 mg, 43%). MS (ES) m/e 376 (M+H)$^+$.

A stirred solution of the above aminoalcohol (520 mg, 1.39 mmole) in CH$_2$Cl$_2$ (10 mL) was treated with triethylamine (0.58 mL, 4.2 mmole) and cooled in and ice bath. Triphosgene (137 mg, 0.46 mmole) was then added slowly, and the mixture was stirred in the ice bath an additional 2 hours. After dilution with chloroform, washing with saturated aqueous NaHCO$_3$ solution and drying over MgSO₄, the mixture was filtered, evaporated and chromatographed on silica using a gradient of 0-10% MeOH/CHCl₃ to afford the product as a white solid (400 mg, 72%) MS (ES) m/e 402 (M+H)⁺.

A solution of the above carbamate (400 mg, 1 mmole) in CHCl₃ (2 mL) was diluted with 4N HCl in dioxane (6 mL), stirred for 1 hour, then evaporated to dryness to give the product (R)-3-(3-amino-propyl)-5-(6-methoxy-quinolin-4-yl)-oxazolidin-2-one as the dihydrochloride salt as a pale yellow solid (375 mg, 100%) MS (ES) m/e 302 (M+H)⁺.

A suspension of the above amine dihydrochloride (150 mg, 0.4 mmole) in CHCl₃ (4 mL) was treated with triethylamine (0.28 mL, 2 mmole) and was cooled in and ice bath. 3-Oxo-3,4-dihydro-2H-benzo[1,4]thiazine-6-sulfonyl chloride (127 mg, 0.48 mmole) was then added and the mixture was stirred for 1 hour with continued cooling. After dilution with chloroform, washing with saturated aqueous NaHCO₃ solution and drying over MgSO₄, the mixture was filtered, evaporated and chromatographed on silica using a gradient of 0-10% MeOH/CHCl₃ to afford 3-Oxo-3,4-dihydro-2H-benzo[1,4]thiazine-6-sulfonic acid {3-[(R)-5-(6-methoxy-quinolin-4-yl)-2-oxo-oxazolidin-3-yl]-propyl}-amide as a white solid (170 mg, 80%) mp: 135-140° C.

NMR δH(CDCl3, 200 MHz): 9.11 (1H, br), 8.77 (1H, d), 8.10 (1H, d), 7.50-7.30 (5H, m), 6.85 (1H, d), 6.14 (1H, dd), 5.69 (1H, t), 4.29 (1H, t), 3.93 (3H, s), 3.47 (2H, s), 3.46-3.32 (3H, m), 2.92 (2H, m), 1.79 (2H, m). MS (ES) m/e 529 (M+H)⁺.

Examples 2, 3, and 4 were prepared in a similar manner:

Example 2

4-Oxo-2,3,4,5-tetrahydro-benzo[b][1,4]thiazepine-7-sulfonic acid {3-[(R)-5-(6-methoxy-quinolin-4-yl)-2-oxo-oxazolidin-3-yl]-propyl}-amide mp: 128-130° C.
NMR δH(CDCl3, 200 MHz): 8.76 (1H, d), 8.37 (1H, s), 8.10 (1H, d), 7.71 (1H, d), 7.63-7.38 (4H, m), 6.85 (1H, d), 6.13 (1H, dd), 5.84 (1H, t), 4.29 (1H, t), 3.93 (3H, s), 3.58-3.30 (5H, m), 2.97 (2H, m), 2.67 (2H, t), 1.96-1.68 (2H, m).

Example 3

3-Oxo-3,4-dihydro-2H-benzo[1,4]oxazine-6-sulfonic acid {3-[(R)-5-(6-methoxy-quinolin-4-yl)-2-oxo-oxazolidin-3-yl]-propyl}-amide mp: 150-155° C.
NMR δH(CDCl3, 200 MHz): 9.23 (1H, s), 8.76 (1H, d), 8.09 (1H, d), 7.51-7.38 (3H, m), 7.39 (1H, d), 7.02 (1H, d), 6.85 (1H, d), 6.15 (1H, dd), 5.53 (1H, t), 4.69 (2H, s), 4.29 (1H, t), 3.93 (3H, s), 3.53-3.31 (3H, m), 2.88 (2H, q), 1.77 (2H, m).

Example 4

7-Chlor-3-oxo-3,4-dihydro-2H-benzo[1,4]thiazine-6-sulfonic acid {3-[(R)-5-(6-methoxy-quinolin-4-yl)-2-oxo-oxazolidin-3-yl]-propyl}-amide mp: 165-170° C.
NMR δH(DMSO-d6, 200 MHz): 10.85 (2H, br), 8.77 (1H, d), 8.01 (1H, d), 7.65 (1H, s), 7.58 (1H, s), 7.55-7.38 (2H, m), 7.20 (1H, d), 3.36 (1H, dd), 4.29 (1H, t), 3.94 (3H, s), 3.56 (2H, s), 3.48-3.09 (3H, m), 2.82 (2H, t), 1.64 (2H, m).

Example 5

3-Oxo-3,4-dihydro-2H-benzo[1,4]thiazine-6-sulfonic acid {3-[(R)-5-(8fluoro-6-methoxy-quinolin-4-yl)-2-oxo-oxazolidin-3-yl]-propyl}-amide (a) 3-fluoro-4-nitroanisole 28 g (0.2 mole) of 3-fluoro-4-nitrophenol was dissolved in 200 mL of acetone. 56 g (0.4 mole) of K₂CO₃ was added, and the contents heated to 40 C for 10 min. Contents were cooled to 0 C, 25 mL (0.4 mole) of methyl iodide added, and again heated to 40 C for 3 hrs. Reaction cooled to rt, roto-evaporated to approx. 100 mL, and 200 mL of methylene chloride was added. Contents were filtered, and the filtrant was rotary-evaporated to dryness. The crystalline solid was recrystallized from 4:1 EtOH/H₂O to give 23.6 g (46%) of desired product. ¹H NMR (CDCl₃, 400 MHz) 8.12 (m, 1H), 6.78 (m, 2H), 3.93 (s, 3H); LCMS (M+H)⁺ 172 found.

(b) 2-fluoro-4-methoxyaniline 30 g (0.175 mole) of 3-fluoro-4-nitroanisole was dissolved in 100 mL of ethanol and degassed several times from alternating vacuum/N₂. 1.5 g of Pd/C was added and the contents were hydrogenated using a Parr shaker (35 psi). After 30 min. the pressure had dropped to 5 psi, so it was increased to 35 psi and allowed to react for another 2 hrs. No further pressure drop was experienced. Contents were degassed, filtered through Celite and rotoary-evaporated to dryness to give 23.4 g (95%) of desired product. No purification was necessary. ¹H NMR (CDCl₃, 400 MHz) 6.71 (dd, 1H), 6.62 (d, 1H), 6.53 (d, 1H) 3.73 (s, 3H), 3.43 (bs, 2H).

(c) 5-[(2-Fluoro-4-methoxy-phenylamino)-methylent]-2,2-dimethyl-[1,3]dioxane-4,6-dione 23.4 g (0.166 mole) of 2-fluoro-4-methoxyaniline, 27.5 g (0.19 mole) of Meldrum's acid, 27.6 mL (0.166 mole) of triethylorthoformate and 135 mL of ethanol were combined and heated to 80 C for 3 hrs. The contents were cooled to rt, and the precipitate which had formed was filtered off and washed with ethanol. The solid was dried in a vacuum oven overnight at 30 C. Yield 43.9 g (90%). ¹H NMR (DMSO, 400 MHz) 8.56 (d, 1H), 7.76 (m, 1H), 7.07 (d, 1H) 6.86 (m, 1H), 3.79 (S, 3H), 1.68 (s, 6H)

(d) 8-Fluoro-6-methoxy-1H-quinolin-4-one 150 mL of Dowtherm A was brought to reflux. To this was added 22 g (74.5 mmol) of 5-[(2-Fluoro-4-methoxy-phenylamino)-methylent]-2,2-dimethyl-[1,3]dioxane-4,6-dione. After addition was complete, the contents were allowed to heat at reflux for another 5 min. during which the reaction durns very dark. Contents were then cooled to room temperature, during which a brown precipitate formed. The contents were diluted with 200 mL of ethyl ether and filtered. The solid precipitate was washed with copious amounts of ethyl ether and dried under vacuum to afford 14.2 g (49%) of product. ¹H NMR (DMSO, 400 MHz) 7.81 (bs, 1H), 7.33 (m, 2H), 6.05 (d, 1H), 3.85 (s, 3H)

(e) 1,1,1-Trifluoro-methanesulfonic acid 8-fluoro-6-methoxy-quinolin-4-yl ester 14 g (72.2 mmol) of 8-Fluoro-6-methoxy-1H-quinolin-4-one was dissolved in 150 mL DMF. The contents were cooled to 0 degrees C. and 3.5 g (86.6 mmol) of NaH (60% susp. in oil) was added. Contents were allowed to stir at 0 degrees C. for 10 min. 30.9 g (86.6 mmol) of phenyl trifluorosulfinimide was added, the ice bath removed, and the contents allowed to stir overnight under inert atmosphere. the reaction was concentrated by rotary evaportation to remove as much DMF as possible, and poured into 500 mL of water. The aqueous contents were extracted (3×25 mL) with ethyl acetate. The organic layers were combined and washed (2×300 mL) with water and (2×300 mL) with brine. The organic layer was dried over sodium sulfate, filtered and rotary-evaporated to dryness. The crude material was purified by flash chromatography on silica gel using 20% ethyl acetate/hexanes as the eluent to give the product 15.8 g (67%). $^1$H NMR (CDCl$_3$, 400 MHz) δ8.85 (d, 1H), 7.45 (d, 1H), 7.21 (d, 1H), 7.08 (s, 1H), 3.97 (s, 3H). LCMS (M+H)$^+$ 326.

(f) 4-(1-Butoxy-vinyl)-8-fluoro-6-methoxy-quinoline 15.5 g (47.5 mmol) of 1,1,1-Trifluoro-methanesulfonic acid 8-fluoro-6-methoxy-quinolin-4-yl ester, 24.5 mL (0.19 mol) of butyl vinyl ether and 13.3 mL of triethylamine were takent up in 100 mL of DMF. 2.0 g (4.75 mmol) of dppp (1,3-bis(diphenylphosphino)propane) and 1.06 g (4.75 mmol) of Pd(OAc)$_2$ were added and the contents heated to 60 C for 4 hrs. No starting material remained. Contents were rotary-evaporated to remove as much DMF as possible. Crude material was purified by flash chromatography on silica gel using 10% ethyl acetate/hexanes as the eluent to give 9.0 g (69%) of the desired product. $^1$H NMR (CDCl$_3$, 400 MHz) 8.78 (d, 1H), 7.43 (d, 1H), 7.28 (m, 1H), 7.09 (d, 1H), 4.58 (d, 1H), 4.50 (d, 1H), 3.96 (t, 2H), 3.90 (s, 3H), 1.80 (m, 2H), 1.53 (m, 2H), 0.97 (t, 3H LCMS (M+H)$^+$ 276.

(g) 2-Bromo-1-(8-fluoro-6-methoxy-quinolin-4-yl)-ethanone 9.0 g (32.7 mmol) of 4-(1-Butoxy-vinyl)-8-fluoro-6-methoxy-quinoline was dissolved in 200 mL of 3:1 THF/water. 6.4 g of N-bromosuccinimide was added and the contents stirred at rt for 3 hrs. Solvent was then removed by rotary-evaporation. The crude material was purified by flash chromatography on silica gel using 20% ethyl acetate/hexanes as the eluent to give 8.5 g (88%) of the desired product. $^1$H NMR (CDCl$_3$, 400 MHz) 8.92 (d, 1H), 7.71 (m, 2H), 7.18 (d, 1H), 4.55 (s, 2H), 3.94 (s, 3H).

(h) (R)-2-Bromo-1-(8-fluoro-6-methoxy-quinolin-4-yl)-ethanol 8.0 g (26.8 mmol) of 2-Bromo-1-(8-fluoro-6-methoxy-quinolin-4-yl)-ethanone was dissolved in 200 mL of toluene. 17.2 g (53.6 mmol) of (+)-DIP-chloride was added and the contents were allowed to stir at rt overnight (16 hrs). 8 mL (80.4 mmol) of diethanolamine was added and the contents were allowed to stir at rt for 3 hrs. The contents were filtered and the solids washed; first with hot toluene, then with ethyl acetate until the washings no longer had UV activity. The crude material was preadsorbed onto silica gel and purified by flash chromatography using 2:1 hexanes/ethyl acetate and going to 100% ethyl acetate afforded 7.95 g (98%) of the product. $^1$H NMR (DMSO, 400 MHz) 8.81 (d, 1H), 7.71 (d, 1H), 7.39 (d, 1H), 7.30 (s, 1H), 6.28 (d, 1H), 5.75 (m, H), 4.00 (s, 3H), 3.97 (dd, 1H), 3.91 (dd, 1H). LCMS (M+H)$^+$ 300. Enantiomeric excess was determined by chiral HPLC to be ≧94%.

(i) 8-Fluoro-6-methoxy-4-(R)-oxiranyl-quinoline 7.75 g (25.8 mmol) of (R)-2-Bromo-1-(8-fluoro-6-methoxy-quinolin-4-yl)-ethanol was dissolved in 200 mL of methanol. 4.0 g (28.5 mmol) of potassium carbonate was added and the contents stirred at rt for 3 hrs. The solids were filtered off, and the resulting solution was rotary-evaporated to dryness. The resulting crude material was partitioned between 600 mL 1:1 ethyl acetate and water. The organic layer was set aside, and the aqueous layer was washed an additional time with 200 mL of ethyl acetate. The organic layers were combined, dried over sodium sulfate, filtered and rotary-evaporated to dryness. The crude material was purified by flash chromatography on silica gel using 25% ethyl acetate/hexanes and going to 60% ethyl acetate/hexanes provided the product 4.2 g (74%). $^1$H NMR (DMSO, 400 MHz) 8.75 (d, 1H), 7.37 (m, 3H), 4.71 (t, 1H), 3.96 (s, 3H), 3.35 (dd, 1H), 2.83 (dd, 1H). LCMS (M+H)$^+$ 220.

8-Fluoro-6-methoxy-4-(R)-oxiranyl-quinoline was converted to the title compound 3-Oxo-3,4-dihydro-2H-benzo[1,4]thiazine-6-sulfonic acid {3-[(R)-5-(8-fluoro-6-methoxy-quinolin-4-yl)-2-oxo-oxazolidin-3-yl]-propyl}-amide using the sequence and methodology descibed in the previous examples.

$^1$H NMR (400 MHz, MeOH-d4): 8.68 (d, J=4.6 Hz, 1H), 7.51 (d, J=4.6 Hz, 1H), 7.30 (d, J=8.0 Hz, 1H), 7.21 (s, 1H), 7.20 (s, 1H), 7.18 (d, J=8.0 Hz, 1H), 6.89 (s, 1H), 6.19 (m, 1H), 4.65 (s, 2H), 3.80 (s, 3H), 3.20-3.31 (m, 4H), 2.71-2.82 (m, 2H), 1.56-2.73 (m, 2H), MS (ES) m/e 547.0 (M+H)$^+$.

Example 6

3-Oxo-3,4-dihydro-2H-benzo[1,4]thiazine-6-sulfonic acid {3-[(R)-5-(6-methoxy-[1,5]naphthyridin-4-yl)-2-oxo-oxazolidin-3-yl]-propyl}-amide (a) 6-methoxy-1H-[1,5]naphthyridin-4-one A solution of 5-amino-2-methoxypyridine (50 g, 0.4 mol) in ethanol (300 ml) was treated with 2,2-dimethyl-[1,3]dioxane-4,6-dione (Meldrum's acid) (68 g) and triethylorthoformate (66 ml). The mixture was heated to reflux for 2 hours, then allowed to cool. Filtration afforded the intermediate 5-[(6-methoxy-pyridin-3-ylamino)-methylene]-2,2-dimethyl-[1,3]dioxane-4,6-dione as a white solid (101.2 g). A portion of this material (50 g) was added to boiling Dowtherm A (300 ml) over 3 minutes under a stream of argon. The mixture was refluxed for a further 5 minutes then allowed to cool before adding to ether. Filtration and drying afforded 6-methoxy-1H-[1,5]naphthyridin-4-one as a white solid (24.7 g, 70%).

MS (+ve ion electrospray) m/z 177 (MH+).

(b) 1,1,1-Trifluoro-methanesulfonic acid 6-methoxy-[1,5]naphthyridin-4-yl ester

A suspension of naphthyridone (a) (10 g, 0.057 mol) in dichloromethane (200 ml) containing 2,6-lutidine (9.94 ml, 86 mmol) and 4-dimethylaminopyridine (0.07 g, 5.7 mol) was cooled in ice and treated with trifluoromethanesulfonic anhydride (10.5 ml, 63 mmol). After stirring for 2.5 hours the mixture was washed with saturated ammonium chloride solution, dried, evaporated and purified on silica eluting with dichloromethane affording the triflate as an oil (13.4 g, 76%).

MS (+ve ion electrospray) m/z 309 (MH+).

(c) (R)-2-Bromo-1-(6-methoxy-[1,5]-naphthyridin-4-yl)ethanol

The triflate (13.2 g, 0.044 mol) in DMF (200 ml) with triethylamine (12 ml, 0.086 mol) butyl vinyl ether (22 ml, 0.17 mol), palladium (II) acetate (0.97 g, 0.0044 mol) and 1,3-bis(diphenylphosphino)propane (1.77 g, 0.0044 mol) was heated at 60° C. for 3 hours then evaporated and chromatographed on silica gel (dichloromethane) to give a yellow solid (10.7 g, 95%). This was dissolved in THF (250 ml), water (40 ml) and treated with N-bromosuccinimide (7.4 g. 0.042 mol) for 1 hour, then evaporated and chromatographed on silica gel (dichloromethane) to give the ketone (10.42 g, 98%).

The ketone (6.6 g, 0.023 mol) in toluene was treated with (+)-B-chlorodiisopinocamphenylborane ((+)-DIP-chloride) (12 g, 0.037 mol) and stirred overnight, then diethanolamine (15 g, 0.14 mol) added and the mixture stirred for 3 hours, filtered and evaporated. Chromatography on silica gel (ethyl acetate-hexane) gave a white solid (4.73 g, 73%).

(e) (R)-2-(6-Methoxy-[1,5]-naphthyridin-4-yl)oxirane

The alcohol (d) (4.8 g, 0.017 mol) in methanol (20 ml) was stirred with potassium carbonate (2.6 g, 0.019 mol) for 1 hour, then evaporated and chromatographed on silica gel (ethyl acetate-hexane-dichloromethane) to give a solid (3.14 g, 92%), (91% ee by chiral HPLC).

MS (+ve ion electrospray) m/z 203 (MH+).

Substituting (+)-B-chlorodiisopinocamphenylborane ((+)-DIP-chloride) with (−)-B-chlorodiisopinocamphenylborane ((−)-DIP-chloride) afforded the antipode in similar enantiomeric excess.

(R)-2-(6-Methoxy-[1,5]-naphthyridin-4-yl)oxirane was converted to the title compound 3-Oxo-3,4-dihydro-2H-benzo[1,4]thiazine-6-sulfonic acid {3-[(R)-5-(6-methoxy-[1,5]naphthyridin-4-yl)-2-oxo-oxazolidin-3-yl]-propyl}-amide using the sequence and methodology describe above.

$^1$H NMR (400 MHz, CDCl$_3$): 8.96 (s, 1H); 8.79 (d, J=4.5 Hz, 1H); 8.25 (d, J=9.1 Hz, 1H); 7.60 (d, J=4.5 Hz, 1H); 7.45 (s, 2H); 7.38 (s, 1H); 7.16 (d, J=9.1 Hz, 1H); 6.33 (m, 1H); 5.71 (m, 1H); 4.36 (t, J=9.2 Hz, 1H); 4.03 (s, 3H); 3.49 (s, 2H); 3.40-3.48 (m, 3H); 2.93 (m, 2H); 1.80-2.05 (m, 2H). MS (ES) m/e 530 (M+H)$^+$.

Example 7

3-Oxo-3,4-dihydro-2H-benzo[1,4]thiazine-6-sulfonic acid {3-[(S)-5-(6- methoxy-[1,5]naphthyridin-4-yl)-2-oxo-oxazolidin-3-yl]-propyl}-amide $^1$H NMR (400 MHz, CDCl$_3$): 8.96 (s, 1H); 8.79 (d, J=4.5 Hz, 1H); 8.25 (d, J=9.1 Hz, 1H); 7.60 (d, J=4.5 Hz, 1H); 7.45 (s, 2H); 7.38 (s, 1H); 7.16 (d, J=9.1 Hz, 1H); 6.33 (m, 1H); 5.71 (m, 1H); 4.36 (t, J=9.2 Hz, 1H); 4.03 (s, 3H); 3.49 (s, 2H); 3.40-3.48 (m, 3H); 2.93 (m, 2H); 1.80-2.05 (m, 2H). MS (ES) m/e 530 (M+H)$^+$.

Example 8

3-Oxo-3,4-dihydro-2H-benzo[1,4]oxazine-6-sulfonic acid {3-[(R)-5-(6-methoxy-[1,5]naphthyridin-4-yl)-2-oxo-oxazolidin-3-yl]-propyl}-amide $^1$H NMR (400 MHz, DMSO-d$_6$): 8.81 (s 1H), 8.40 (d, J=4.3 Hz, 1H), 7.87 (d, J=9.0 Hz, 1H), 7.23 (d, J=4.3 Hz, 1H), 7.06 (d, J=8.3 Hz, 1H), 6.95 (s, 1H), 6.86 (s, 1H), 6.78 (d, J=9.0 Hz, 1H), 6.65 (d, J=8.3 Hz, 1H), 6.05 (m, 1H), 5.40 (m, 1H), 4.35 (s, 2 H), 3.95 (m, 1H), 3.75 (s, 3H), 2.80-3.21 (m, 2H), 1.30-1.62 (m, 4H), MS (ES) m/e 515.0 (M+H)$^+$.

The amide compounds were prepared as above using (R)-3-(3-amino-propyl)-5-(6-methoxy-quinolin-4-yl)-oxazolidin-2-one dihydrochloride and the appropriate acid chloride in place of the sufonyl chloride.

Example 9

3-Oxo-3,4-dihydro-2H-pyrido[3,2-b][1,4]thiazine-6-carboxylic acid {3-[(R)-5-(6-methoxy-quinolin-4-yl)-2-oxo-oxazolidin-3-yl]-propyl}-amide A suspension of (R)-3-(3-amino-propyl)-5-(6-methoxy-quinolin-4-yl)-oxazolidin-2-one amine dihydrochloride (74 mg, 0.19 mmole) in CHCl$_3$ (3 mL) was treated with triethylamine (0.11 mL, 0.9 mmole) and was cooled in and ice bath. 3-Oxo-3,4-dihydro-2H-pyrido[3,2-b][1,4]thiazine-6-carbonyl chloride (53 mg, 0.23 mmole) was then added and the mixture was stirred for 1 hour with continued cooling. After dilution with chloroform, washing with saturated aqueous NaHCO$_3$ solution and drying over MgSO$_4$, the mixture was filtered, evaporated and chromatographed on silica using a gradient of 0-10% MeOH/CHCl$_3$ to afford the product as an off-white solid (60 mg, 61%)

NMR δH(CDCl3, 400 MHz): 8.79 (d, J=4.5 Hz, 1H); 8.44 (bs, 1H); 8.18 (m, 1H); 8.10 (d, J=9.3 Hz, 1H); 7.74-7.80 (m, 2H); 7.52 (d, J=4.5 Hz, 1H); 7.43 (dd, J=9.3, 2.6 Hz, 1H); 6.88 (d, J=2.6 Hz, 1H); 6.14 (m, 1H); 3.97 (s, 3H); 3.53 (s, 2H); 3.38-3.51 (m, 6H); 1.80-1.87 (m, 2H). MS (ES) m/e 494 (M+H)$^+$.

The amines were prepared from (R)-3-(3-amino-propyl)-5-(6-methoxy-quinolin-4-yl)-oxazolidin-2-one amine and the appropriate aldehyde using a reductive amination sequence.

Example 10

(R)-3-{3-[(1H-Indol-2-ylmethyl)-methyl-amino]-propyl}-5-(6-methoxy-quinolin-4-yl)-oxazolidin-2-one

(a) {3-[(R)-2-Hydroxy-2-(6-methoxy-quinolin-4-yl)-ethylamino]-propyl}-methyl-carbamic acid dimethyl-ethyl ester A mixture of 6-methoxy-4-(R)-oxiranyl-quinoline (0.9 g, 4.47 mmol), (3-amino-propyl)-methyl-carbamic acid dimethyl-ethyl ester [150349-36-3] (0.99 g, 5.25 mmol), lithium perchlorate (0.49 g, 4.6 mmol) and anhydrous acetonitrile (10 ml) was stirred under argon, at room temperature, for 3 days. The solvent was concentrated and the residue was dissolved in ethyl acetate. The organic phase was washed twice with water, dried over magnesium sulfate and concentrated. The residue was chromatographed on silicagel eluting with methylene chloride-methanol (first 95-5, then 90-10) to give (3-

[(R)-2-hydroxy-2-(6-methoxy-quinolin-4-yl)-ethylamino]-propyl}-methyl-carbamic acid dimethyl-ethyl ester (0.84 g, 48%).

NMR δH(CDCl3, 200 MHz): 8.76 (1H, d), 8.02 (1H, d), 7.62 (1H, d), 7.36 (1H, dd), 7.24 (1H, m), 5.64 (1H, m), 3.96 (3H, s), 3.49-3.10 (3H, m), 2.96-2.60 (3H, m), 2.84 (3H, s), 2.17 (1H, br), 1.85 (2H, m), 1.43 (9H, s).

(b) {3-[(R)-5-(6-Methoxy-quinolin-4-yl)-2-oxo-oxazolidin-3-yl]-propyl}-methyl-carbamic acid dimethyl-ethyl ester A mixture of {3-[(R)-2-hydroxy-2-(6-methoxy-quinolin-4-yl)-ethylamino]-propyl}-methyl-carbamic acid dimethyl-ethyl ester (830 mg, 2.1 mmol), 4 (dimethylamino)pyridine (DMAP) (329 mg, 2.66 mmol), 1,1'-carbonyldiimidazole (CDI) (454 mg, 2.77 mmol) and methylene chloride stabilized over amylene (20 ml) was stirred under argon, at room temperature, for 4 days. The solution was washed with water, dried over magnesium sulfate and concentrated. The residue was chromatographed on silicagel eluting with methylene chloride-methanol (95-5) to give {3-[(R)-5-(6-methoxy-quinolin-4-yl)-2-oxo-oxazolidin-3-yl]-propyl}-methyl-carbamic acid dimethyl-ethyl ester (770 mg, 88%).

NMR δH(CDCl3, 200 MHz): 8.82 (1H,d), 8.14 (1H, d), 7.59 (1H, d), 7.45 (1H, dd), 6.90 (1H, d), 6.12 (1H, dd), 4.32 (1H, m), 3.97 (3H, s), 3.53-3.08 (5H, m), 2.83 (3H, s), 1.79 (2H, m), 1.41 (9H, s).

(c) (R)-5-(6-Methoxy-quinolin-4-yl)-3-(3-methylamino-propyl)-oxazolidin-2-one

A mixture of 3-[(R)-5-(6-methoxy-quinolin-4-yl)-2-oxo-oxazolidin-3-yl]-propyl)-methyl-carbamic acid dimethyl-ethyl ester (760 mg, 1.83 mmol), trifluoroacetic acid (5 ml) and methylene chloride (10 ml) was stirred for 2 hours at room temperature. The solvent was concentrated and the residue was dissolved in water, made neutral with a 15% sodium hydroxide solution and finally extracted twice with methylene chloride. The organic phase was dried over magnesium sulfate and concentrated to dryness to give (R)-5-(6-methoxy-quinolin-4-yl)-3-(3-methylamino-propyl)-oxazolidin-2-one (470 mg, 81%).

NMR δH(CDCl3, 200 MHz): 8.81 (1H, d), 8.10 (1H, d), 7.55 (1H, d), 7.43 (1H, dd), 6.88 (1H, d), 6.15 (1H, dd), 4.31 (1H, t), 3.96 (3H, s), 3.60-3.28 (3H, m), 2.71 (2H, t), 2.48 (3H, s), 2.15 (1H, br), 1.85 (2H, m).

(d) (R)-3-{3-[(1H-Indol-2-ylmethyl)-methyl-amino]-propyl}-5-(6-methoxy-quinolin-4-yl)-oxazolidin-2-one Acetic acid (30 ul, 0.475 mmol) was added to a solution of (R)-5-(6-methoxy-quinolin-4-yl)-3-(3-methylamino-propyl)-oxazolidin-2-one (150 mg, 0.475 mmol) and 1H-indole-2-carbaldehyde [19005-93-7] (72 mg, 0.475 mmol) in methylene chloride stabilized over amylene (4.5 ml) and the mixture was stirred for 30 minutes. Sodium triacetoxyborohydride (230 mg, 1.01 mmol) was then added and stirring was maintained for 48 hours at room temperature. Then water (5 ml) was added, the organic phase was decanted, washed with water dried over magnesium sulfate and concentrated. The residue was chromatographed on silicagel eluting with methylene chloride-methanol (9-1) to give a first crop of pure (R)-3-{3-[(1H-indol-2-ylmethyl)-methyl-amino]-propyl}-5-(6-methoxy-quinolin-4-yl)-oxazolidin-2-one (18 mg) and a less pure fraction of 90 mg (estimated yield >50%).

NMR δH(CDCl3, 200 MHz): 9.55 (1H, br), 8.64 (1H, d), 8.09 (1H, d), 7.62-7.35 (3H, m), 7.25 (1H, d), 7.21-7.02 (2H, m), 6.80 (1H, d), 6.32 (1H, m), 5.98 (1H, dd), 4.10 (1H, t), 3.94 (3H, s), 3.70 (2H, d), 3.53-3.27 (3H, m), 2.42 (2H, m), 2.25 (3H, s), 1.72 (2H, m).

The following is a representative example of the reductive amination procedure.

Example 11

(R)-3-{3-[(Benzo[1,2,5]thiadiazole-5-ylmethyl)-amino]-propyl}-5-(6-methoxy-quinolin-4-yl)-oxazolidin-2-one A mixture of (R)-3-(3-amino-propyl)-5-(6-methoxy-quinolin-4-yl)-oxazolidin-2-one (0.15 g, 0.5 mmol), benzo[1,2,5]thiadiazole-5-carbaldehyde (92 mg, 0.56 mmol), methanol (0.5 ml), methylene chloride (1.8 ml), 3 Å dry molecular sieve (1 g) was stirred at room temperature for 16 hours. Sodium borohydride (28 mg, 0.76 mmol) was added and the mixture was stirred for 3 hours. After concentration of the solvent the residue was dissolved in ethyl acetate and the organic phase was washed with water, dried over magnesium sulfate and concentrated. The residue was chromatographed on silicagel eluting with methylene chloride-methanol (99-1 first, then 90-10) to give (R)-3-{3-[(benzo[1,2,5]thiadiazol-5-ylmethyl)-amino]-propyl}-5-(6-methoxyquinolin-4-yl)-oxazolidin-2-one (150 mg, 59%).

NMR δH(CDCl3, 200 MHz): 8.77 (1H, d), 8.10 (1H, d), 7.94 (1H, d), 7.88 (1H, d), 7.58 (1H, dd), 7.52 (1H, dd), 7.42 (1H, dd), 6.85 (1H, d), 6.10 (1H, dd), 4.23 (1H, t), 3.94 (3H, s), 3.93 (2H, s), 3.53-3.37 (3H, m), 2.68 (2H, t), 1.78 (2H, m), 1.71 (1H, br).

Examples 12-19 were prepared by the same method:

Example 12

(R)-3-{3-[(1H-Indol-2-ylmethyl)-amino]-propyl}-5-(6-methoxy -quinolin-4-yl) -oxazolidin-2-one NMR δH(CDCl3, 200 MHz): 9.44 (1H, br), 8.53 (1H,d), 8.06 (1H, d), 7.62-7.35 (3H, m), 7.25-6.99 (3H, m), 6.79 (1H, d), 6.36 (1H, d), 6.05 (1H, dd), 4.13 (1H, t), 4.07 (2H, m), 3.92 (3H, s), 3.58-3.20 (3H, m), 2.63 (2H, m), 2.49 (1H, br), 1.75 (2H, m).

Example 13

(R)-3-{3-[(8-Hydroxy-quinolin-2-ylmethyl)-methyl-amino]-propyl}-5-(6-methoxy-quinolin-4-yl)-oxazolidin-2-one NMR δH(CDCl3, 200 MHz): 8.71 (1H, d), 8.15-7.96 (2H, 2d), 7.59-7.20 (5H, m), 7.10 (1H, m), 6.81 (1H, d), 5.97 (1H, dd), 4.15 (1H, t), 3.90 (3H, s), 3.73 (2H, s), 3.50-3.23 (3H, m), 2.80 (1H, br), 2.46 (2H, m), 2.23 (3H, s), 1.75 (2H, m).

Example 14

(R)-3-{3-[(4-Fluoro-1H-benzoimidazol-2-ylmethyl)-amino]-propyl}-5-(6-methoxy-quinolin-4-yl)-oxazolidin-2-one NMR δH(DMSO-d6, 200 MHz): 8.73 (1H,d), 8.01 (1H, d), 7.47 (1H, dd), 7.43 (1H, d), 7.28 (1H, d), 7.20 (1H, d), 7.09 (1H, m), 6.91 (1H, dd), 6.38 (1H, dd), 4.29 (1H, t), 3.92 (3H, s), 3.88 (2H, s), 3.65-3.10 (4H, m, br), 2.50 (2H, t), 1.65 (2H, m).

Example 15

6-({3-[(R)-5-(6-Methoxy-quinolin-4-yl)$_2$-oxo-oxazolidin-3-yl]-propylamino}-methyl-4H-benzo[1,4]oxazin-3-one NMR δH(DMSO-d6, 200 MHz): 10.65 (1H, br), 8.77 (1H, d), 8.01 (1H, d), 7.55-7.39 (2H, m), 7.20 (1H, d), 6.91-6.78 (3H, m), 6.38 (1H, dd), 4.51 (2H, s), 4.32 (1H, t), 3.94 (3H, s), 3.54 (2H, s), 3.50-3.12 (4H, m,br), 2.45 (2H, t), 1.63 (2H, m).

Example 16

(R)-3-{3-[(8-Hydroxy-quinolin-2-ylmethyl)-amino]-propyl}-5-(6-methoxy-quinolin-4-yl)-oxazolidin-2-one NMR δH(CDCl3, 200 MHz): 8.69 (1H, d), 8.10 (2H, 2d), 7.55-7.26 (5H, m), 7.18 (1H, dd), 6.85 (1H, d), 6.14 (1H, dd), 4.28 (1H, t), 4.14 (2H, m), 3.94 (3H, s), 3.58-3.33 (3H, m), 2.80 (2H, t), 2.28 (2H, br), 1.89 (2H, m).

Example 17

(6-({3-[(R)-5-(6-Methoxy-quinolin-4-yl)-2-oxo-oxazolidin-3-yl]-propylamino}-methyl-4H-benzo[1,4]thiazin-3-one NMR δH(CDCl3, 200 MHz): 8.75 (1H, d), 8.35 (1H, br), 8.10 (1H, d), 7.50-7.38 (2H, m), 7.23 (1H, d), 6.97-6.80 (3H, m), 6.10 (1H, dd), 4.20 (1H, t), 3.94 (3H, s), 3.70 (2H, s), 3.54-3.30 (5H, m), 2.55 (2H, t), 1.71 (3H, m,br).

Example 18

6-({3-[(R)-5-(6-Methoxy-quinolin-4-yl)-2-oxo-oxazolidin-3-yl]-propylamino}-methyl)-4H-pyrido[3,2-b][1,4]oxazin-3-one dihydrochloride $^1$H NMR (400 MHz, MeOH-d4): 9.05 (d, J=5.6 Hz, 1H); 8.22 (d, J=9.4 Hz, 1H); 8.10 (d, J=5.6 Hz, 1H); 7.87 (dd, J=9.4, 2.5 Hz, 1H); 7.47 (d, J=2.5 Hz, 1H); 7.35 (d, J=7.0 Hz, 1H); 7.08 (d, J=7.0 Hz, 1H); 6.67 (m, 1H); 4.69 (s, 2H); 4.25 (s, 2H); 4.11 (s, 3H); 3.50-3.61 (m 2H); 3.34-3.42 (m, 2H); 3.16-3.31 (m, 2H). MS (ES) m/e 464.0 (M+H)$^+$.

Example 19

6-({3-[(R)-5-(8-Fluoromethoxy-quinolin-4-yl)-2-oxo-oxazolidin-3-yl]-propylamino}-methyl)-4H-pyrido[3,2-b][1,4]oxazin-3-one dihydrochloride $^1$H NMR (400 MHz, MeOH-d4): 8.89 (d, J=4.6 Hz, 1H), 7.98 (d, J=4.6 Hz, 1H), 7.50 (d, J=8.9 Hz, 1H), 7.25 (d, J=8.0, 1H), 7.16 (s, 1H), 7.08 (d, J=8.0 Hz, 1H), 6.49 (m, 1H), 4.65 (s, 2H), 4.15 (s, 2H), 3.88 (s, 3H), 3.12-3.51 (m, 6H), 2.11-2.32 (m, 2 H), MS (ES) m/e 482.0 (M+H)$^+$.

Example 20

(R)-3-3-{[2-(3,5-Difluoro-phenoxy)-ethyl]-methyl-amino}-propyl)-5-(6-methoxy-quinolin-4-yl)-oxazolidin-2-one (a) Methanesulfonic acid 2-(3,5-difluoro-phenoxy)-ethyl ester A solution of 2-(3,5-difluoro-phenoxy)-ethanol (2.5 g, 14.3 mmol) in pyridine (10 ml) was cooled with an ice bath and treated dropwise with methanesulfonyl chloride (1.7 g, 14.7 mmol). The ice bath was removed and the mixture was stirred for 16 hours at room temperature. The pyridine was evaporated in vacuo and the residue was dissolved in ethyl acetate. The organic phase was washed with water, with 2N hydrochloric acid then three times with water, dried over magnesium sulfate and concentrated. The residue was crystallised in diisopropyl ether to give methanesulfonic acid 2-(3,5-difluoro-phenoxy)-ethyl ester (1.8 g, 51%).

NMR δH(CDCl3, 200 MHz): 6.57-6.36 (3H, m), 4.56 (2H, m), 4.21 (2H, m), 3.09 (3H, s).

[2-(3,5-Difluoro-phenoxy)-ethyl]-methyl-amine

A mixture of methanesulfonic acid 2-(3,5-difluoro-phenoxy)-ethyl ester (1.2 g, 4.76 mmol), THF (30 ml) and 40% aqueous monomethylamine (30 ml) was heated under reflux for 8 hours. The reaction mixture was poured on water and extracted 3 times with diethyl ether (3×20 ml). The orghanic phase was washed with water, dried over magnesium sulfate and concentrated to dryness. The residue was chromatographed on silicagel eluting with methylene chloride-methanol (9-1) to give [2-(3,5-difluoro-phenoxy)-ethyl]-methyl-amine (0.63 g, 71%).

NMR δH(CDCl3, 200 MHz): 6.53-6.35 (3H, m), 4.03 (2H, t), 2.96 (2H, t), 2.50 (3H, s), 1.63 (1H, br).

(c) 2-(3-{[2-(3,5-Difluoro-phenoxy)-ethyl]-methyl-amino}-propyl)-isoindole-1,3-dione A mixture of [2-(3,5-difluoro-phenoxy)-ethyl]-methyl-amine (0.63 g, 3.4 mmol), 2-(3-bromo-propyl)-isoindole-1,3-dione (1.03 g, 3.8 mmol), 30% potassium fluoride on Celite® (1.35 g, 7 mmol) and acetonitrile (30 ml) was stirred for 20 hours at 50° C. The solvent was concentrated and the residue was dissolved in ethyl acetate. The Celite was filtered off, the solution was washed with water, then the organic phase was dried over magnesium sulfate and concentrated. The residue was chromatographed on silicagel eluting with methylene chloride-methanol (97-3) to give 2-(3-{[2-(3,5-difluoro-phenoxy)-ethyl]-methyl-amino}-propyl)-isoindole-1,3-dione (1 g, 78.6%).

NMR δH(CDCl3, 200 MHz): 7.90-7.66 (4H, m), 6.50-6.32 (3H, m), 3.99 (2H, t), 3.77 (2H, t), 2.79 (2H, t), 2.56 (2H, t), 2.32 (3H, s), 1.89 (2H, m).

(d) N$^1$-[2-(3,5-Difluoro-phenoxy)-ethyl]-N$^1$-methyl-propane-1,3-diamine

A mixture of 2-(3-([2-(3,5-difluoro-phenoxy)-ethyl]-methyl-amino)-propyl)-isoindole-1,3-dione (1 g, 2.67 mmol), hydrazine hydrate (0.8 ml) and ethanol (20 ml) was heated under reflux for 2 hours. The solvent was concentrated and the residue was suspended in diethyl ether. The solid formed was fileteted off and washed with ether. The filtrated was concentrated to dryness to give N$^1$-[2-(3,5-difluoro-phenoxy)-ethyl]-N$^1$-methyl-propane-1,3-diamine (0.65 g, 99%).

NMR δH(CDCl3, 200 MHz): 6.53-6.31 (3H, m), 4.00 (2H, t), 3.19 (2H, br), 2.85-2.68 (4H, m), 2.51 (2H, t), 2.31 (3H, s), 1.65 (2H, m).

(e) (R)-2-(3-{[2-(3,5-Difluoro-phenoxy)-ethyl]-methyl-amino}-propylamino)-1-(6-methoxy-quinolin-4-yl)-ethanol A mixture of 6-methoxy-4-(R)-oxiranyl-quinoline [RN 314741-44-1] (0.51 g, 2.53 mmol), N$^1$-[2-(3,5-difluoro-phenoxy)-ethyl]-N¹-methyl-propane-1,3-diamine (0.65 g, 2.66 mmol), lithium perchlorate (0.29 g, 2.7 mmol) and anhydrous acetonitrile (5 ml) was stirred at room temperature for 3 days. The solvent was concentrated and the residue was dissolved in ethyl acetate. The solution was washed with water, dried over magnesium sulfate and concentrated to dryness. The residue was chromatographed on silicagel eluting with methylene chloride-methanol-NH$_4$OH (9-1-0.1). The most polar fraction was chromatographed again eluting first with methylene chloride-methanol (9-1) then with methylene chloride-methanol-NH$_4$OH (95-5-0.5) to give (R)-2-(3-{[2-(3,5-difluoro-phenoxy)-ethyl]-methyl-amino}-propylamino)-1-(6-methoxy-quinolin-4-yl)-ethanol (0.15 g, 13.5%).

NMR δH(CDCl3, 200 MHz): 8.70 (1H, d), 7.87 (1H, d), 7.52 (1H, d), 7.19 (1H, dd), 7.06 (1H, d), 6.55-6.30 (3H, m), 5.68 (1H, dd), 4.07 (2H, t), 3.83 (3H, s), 3.16 (1H, dd), 2.91-2.59 (7H, m), 2.42 (3H, s), 2.20 (2H, br), 1.95 (1H, m), 1.72 (1H, m).

(f) (R)-3-(3-{[2-(3,5-Difluoro-phenoxy)-ethyl]-methyl-amino}-propyl)-5-(6-methoxy -quinolin-4-yl)-oxazolidin-2-one A mixture of (R)-2-(3-{[2-(3,5-difluoro-phenoxy)-ethyl]-methyl-amino}-propylamino}-1-(6-methoxy-quinolin-4-yl)-ethanol (105 mg, 0.24 mmol), DMAP-(38 mg, 0.31 mmol), 1,1'-carbonyldiimidazole (51 mg, 0.31 mmol) and methylene chloride stabilised on amylene (4 ml) was stirred at room temperature for 16 hours. The solvent was concentrated and the residue was chromatographed on silicagel eluting with methylene chloride-methanol (94-6) to give (R)-3-(3-{[2-(3,5-difluoro-phenoxy)-ethyl]-methyl-amino)-propyl)-5-(6-methoxy-quinolin-4-yl)-oxazolidin-2-one (70 mg, 62%).

NMR δH(CDCl3, 200 MHz): 8.80 (1H, d), 8.09 (1H, d), 7.55 (1H, dd), 7.42 (1H, dd), 6.91 (1H, d), 6.50-6.32 (3H, m), 6.13 (1H, dd), 4.38 (1H, t), 4.07 (2H, m), 3.96 (3H, s), 3.58-3.23 (3H, m), 2.88 (2H, m), 2.61 (2H, m), 2.41 (3H, s), 1.83 (2H, m).

Example 21

3-Oxo-3,4-dihydro-2H-benzo[1,4]thiazine-6-sulfonic acid{3-[(R)-5-(6-methoxy-[1,5]naphthyridin-4-yl)-2-oxo-oxazolidin-3-yl]-2,2-dimethyl-propyl}-amide A solution of epoxide SB-722846 (0.91 g, 4.5 mmol) and (3-amino-2,2-dimethyl-propyl)-carbamic acid tert-butyl ester (1.0 g, 4.9 mmol) in DMF (5 mL) was heated at 60° C. for 15 hours. Evaporation of the solvent and flash chromatography on silica gel using 90:10 CHCl$_3$:MeOH afforded the aminoalcohol as a dark yellow oil (0.83 g, 46%) MS (ES) m/e 405 (M+H)⁺.

A stirred solution of the above aminoalcohol (0.83 g, 2.05 mmol) in CH$_2$Cl$_2$ (20 mL) was treated with triethylamine (3.0 mL, 21.5 mmol) and cooled to 0° C. Triphosgene (0.21 g, 0.71 mmol) was added and the solution was stirred for 2 hours at 0° C. After dilution with chloroform, the organic phase was washed with saturated aqueous NaHCO$_3$ solution, dried (MgSO$_4$), filtered and concentrated. Flash chromatography on silica gel using a gradient of 0-10% MeOH/CHCl$_3$ afforded the product as a white solid. (0.60 g, 68%) MS (ES) m/e 331 (M−100+H)⁺.

To a solution of the above carbamate (0.21 g, 0.29 mmol) in CHCl$_3$ (1 mL) was added 4N HCl in dioxane (3 mL, 12 mmol) and the reaction mixture was stirred for 1 hour. After evaporation of the solvent, CHCl$_3$ (5 mL) and triethylamine (0.35 mL, 2.5 mmol) were added and the solution cooled to 0° C.

3-Oxo-3,4-dihydro-2H-benzo[1,4]thiazine-6-sulfonyl chloride (RM49215-119A1, 0.17 g, 0.65 mmol) was added and the mixture was stirred for 1 hour with continued cooling. After dilution with chloroform, the organic phase was washed with saturated aqueous NaHCO$_3$ solution, dried (MgSO$_4$), filtered and concentrated. Flash chromatography on silica gel using a gradient of 0-10% MeOH/CHCl$_3$ afforded the product as a white solid. (0.13 g, 48%) ¹H NMR (400 MHz, CDCl3): δ 9.05 (s, 1H); 8.80 (d, J=4.5 Hz, 1H); 8.26 (d, J=9.1 Hz, 1H); 7.59 (d, J=4.2 Hz, 1H); 7.4-7.5 (overlapping signals, 3H); 7.16 (d, J=9.1 Hz, 1H); 6.39 (t, J=7.3 Hz, 1H); 6.31 (m, 1H); 4.43 (t, J=9.3 Hz, 1H); 4.01 (s, 3H); 3.56 (dd, J=9.1, 7.3 Hz, 1H); 3.51 (s, 2H); 3.17 (d, J=14.9 Hz, 1H); 2.98 (d, J=14.7 Hz, 1H); 2.66 (m, 2H); 0.99 (s, 3H); 0.87 (s, 3H). MS (ES) m/e 558 (M+H)⁺.

Example 22

2,3-Dihydro-benzo[1,4]dioxinesulfonic acid {3-[5-(6-methoxy-[1,5]naphthyridin-4-yl)-2-oxo-oxazolidin-3-yl]-propyl}-amide To the dihydrochloride salt of 3-(3-Amino-propyl)-5-(6-methoxy-[1,5]naphthyridin-4-yl)-oxazolidin-2-one (previous patent) (0.17 g, 0.45 mmol) in CHCl$_3$ (5 mL) was added triethylamine (0.37 mL, 2.65 mmol) and the solution was cooled to 0° C. 2,3-Dihydro-benzo[1,4]dioxine-6-sulfonyl chloride (0.14, 0.60 mmol) was added and the mixture was stirred for 1 hour with continued cooling. After dilution with chloroform, the organic phase was washed with saturated aqueous NaHCO$_3$ solution, dried (MgSO$_4$), filtered and concentrated. Flash chromatography on silica gel using a gradient of 0-10% MeOH/CHCl$_3$ afforded the product as a white solid (0.17 g, 75%) ¹H NMR (400 MHz, CDCl$_3$): δ 8.79 (d, J=4.5 Hz, 1H); 8.24 (d, J=9.1 Hz, 1H); 7.65 (d, J=4.5 Hz, 1H); 7.36 (d, J=2.3 Hz, 1H); 7.32 (dd, J=8.5, 2.2 Hz, 1H); 7.16 (d, J=9.1 Hz, 1H); 6.79 (d, J=8.4 Hz, 1H); 6.31 (dd, J=8.7, 7.4 Hz, 1H); 5.37 (t, J=6.6 Hz, 1H); 4.39 (t, J=9.3 Hz, 1H); 4.26-4.32 (m, 4H); 4.05 (s, 3H); 3.32-3.47 (m, 3H); 2.94 (m, 2H); 1.76 (m, 2H). MS (ES) m/e 501 (M+H)⁺.

Example 23

6-({3-[5-(6-Methoxy-[1,5]naphthyridin-4-yl)-2-oxo-oxazolidin-3-yl]-propylamino}-methyl)-4H-pyrido[3,2-b][1,4]thiazin-3-one To the dihydrochloride salt of 3-(3-Amino-propyl)-5-(6-methoxy-[1,5]naphthyridin-4-yl)-oxazolidin-2-one (previous patent) (0.47 g, 1.25 mmol) in CH$_2$Cl$_2$ (14 mL) and MeOH (3.5 mL) was added triethylamine (1.0 mL, 7.2 mmol) and the mixture was stirred at room temperature until all the solid went into solution. 3-Oxo-3,4-dihydro-2H-pyrido[3,2,b][1,4]thiazine-6-carbaldehyde (SB-735214, 0.24 g, 1.24 mmol) was added and the reaction mixture was stirred for 15 hours. Sodium borohydride (0.0519, 1.35 mmol) was added followed by methanol (10 mL). After 30 minutes, the reaction mixture was diluted with chloroform and washed with saturated aqueous NaHCO$_3$ solution, dried (MgSO$_4$), filtered and concentrated. Flash chromatography on silica gel using a gradient of 0-10% MeOH/CHCl$_3$ afforded the product as a white solid (0.32 g, 53%) ¹H NMR (400 MHz, CDCl$_3$): δ8.80 (d, J=4.6 Hz, 1H); 8.36 (d, J=9.1 Hz, 1H); 7.70 (d, J=4.5 Hz, 1H); 7.56 (d, J=7.8 Hz, 1H); 7.17 (d, J=9.1 Hz, 1H); 6.92 (d, J=7.8 Hz, 1H); 6.31 (dd, J=8.6, 6.9 Hz, 1H); 4.35 (t, J=9.3 Hz, 1H); 4.04 (s, 3H); 3.75 (s, 2H); 3.48 (s, 2H); 3.47 (dd, J=8.9, 6.9 Hz, 1H); 3.41 (m, 1H); 2.63 (m, 2H), 1.75 (m, 2H). MS (ES) m/e 481 (M+H)⁺.

Example 24

6-({3-[5-(6-Methoxy-[1,5]naphthyridin-4-yl)-2-oxo-oxazolidin-3-yl]-propylamino}methyl)-4H-pyrido[3,2-b][1,4]oxazin-3-one To the dihydrochloride salt of 3-(3-Amino-propyl)-5-(6-methoxy-[1,5]naphthyridin-4-yl)-oxazolidin-2-one (previous patent) (0.47 g, 1.25 mmol) in $CH_2Cl_2$ (14 mL) and MeOH (3.5 mL) was added triethylamine (1.0 mL, 7.2 mmol) and the mixture was stirred at room temperature until all the solid went into solution. 3-Oxo-3,4-dihydro-2H pyrido[3,2,b][1,4]oxazine-6-carbaldehyde (SB-735368, 0.22 g, 1.23 mmol) was added and the reaction mixture was stirred for 15 hours. Sodium borohydride (0.0519, 1.35 mmol) was added followed by methanol (10 mL). After 30 minutes, the reaction mixture was diluted with chloroform and washed with saturated aqueous $NaHCO_3$ solution, dried ($MgSO_4$), filtered and concentrated. Flash chromatography on silica gel using a gradient of 0-10% MeOH/$CHCl_3$ afforded the product as a white solid (0.36 g, 62%) $^1H$ NMR (400 MHz, $CDCl_3$): 0.8.79 (d, J=4.3 Hz, 1H); 8.26 (d, J=9.1 Hz, 1H); 7.70 (d, J=4.6 Hz, 1H); 7.18 (d, J=8.1 Hz, 1H); 7.17 (dd, J=9.0, 1.0 Hz, 1H); 6.87 (d, J=8.1 Hz, 1H); 6.31 (dd, J=9.0, 7.0 Hz, 1H); 4.64 (s, 2H); 4.35 (t, J=9.1 Hz, 1H); 4.04 (s, 3H); 3.72 (s, 2H); 3.47 (dd, J=8.8, 6.8 Hz, 1H); 3.41 (m, 2H); 2.63 (m, 2H); 1.75 (m, 2H). MS (ES) m/e 465 (M+H)$^+$.

Example 25

3-Oxo-3,4-dihydro-2H-benzo[1,4]thiazine-6-sulfonic acid {(R)-2-hydroxy-3-[(R)-5-(6-methoxy-[1,5]naphthyridin-4-yl)-2-oxo-oxazolidin-3-yl]-propyl}-amide A solution of epoxide SB-722846 (1.4 g, 6.9 mmol) and C-((R)-2,2-dimethyl-[1,3]dioxolan-4-yl)-methylamine (1.0 g, 7.6 mmol) in DMF (10 mL) was heated at 60° C. for 24 hours. Evaporation of the solvent and flash chromatography on silica gel using 90:10 $CHCl_3$:MeOH afforded tha aminoalcohol as an oil (1.0 g, 43%) MS (ES) m/e 334 (M+H)$^+$.

A stirred solution of the above aminoalcohol (1.0 g, 3.3 mmol) in $CH_2Cl_2$ (20 mL) was treated with triethylamine (5 mL, 36 mmol) and cooled to 0° C. Triphosgene (0.36 g, 1.2 mmol) was added and the solution was stirred for 2 hours at 0° C. After dilution with chloroform, the organic phase was washed with saturated aqueous $NaHCO_3$ solution, dried ($MgSO_4$), filtered and concentrated. Flash chromatography on silica gel using a gradient of 0-10% MeOH/$CHCl_3$ afforded the oxazolidinone as an oil (0.74 g, 69%) MS (ES) m/e 360 (M+H)$^+$.

A solution of the above oxazolidinone (0.57 g, 1.6 mmol) in 4N HCl-THF (10 mL conc. HCl+30 mL THF) was stirred at room temperature for 3 hours. $NaHCO_3$ was added slowly until gas evolution stop and the pH was neutral. The aqueous layer was extracted with THF (3×50 mL) and EtOAc (1×25 mL). The extracts were dried ($MgSO_4$), filtered and concentrated. Flash chromatography on silica gel using a gradient of 2-10% MeOH/$CHCl_3$ afforded the diol as a white solid (0.40 g, 79%) MS (ES) m/e 320 (M+H)$^+$.

To a stirred solution of the above diol (0.30 g, 0.94 mmol) in pyridine (6 mL) at 0° C. was added TsCl (0.20 g, 1.05 mmol)). The reaction mixture was stirred for 24 hour with continuing cooling. Triethylamine (0.5 mL) was added and the solution was evaporated. Flash chromatography on silica gel using a gradient of 0-10% MeOH/$CHCl_3$ afforded the tosylate as a pink solid (0.31 g, 70%) MS (ES) m/e 474 (M+H)$^+$.

To a solution of the above tosylate (0.31 g, 0.65 mmol) in DMF (10 mL) was added $NaN_3$ (0.3 g, 4.6 mmol) and NaI (0.02 g, 0.13 mmol). After being stirred at 45° C. for 15 h, the reaction mixture was diluted with water and extracted with chloroform. The extracts were dried ($MgSO_4$), filtered and concentrated. The crude azide [MS (ES) m/e 345 (M+H)$^+$] was dissolved in THF (10 mL) and water (1 mL). $PPh_3$ (0.34 g, 1.30 mmol) was added and the reaction mixture was stirred for 20 hours at room temperature. The solvents were evaporated and the crude mixture was evaporated from toluene to remove traces of water. Evaporation of the solvent and flash chromatography on silica gel using 80:20:2 $CHCl_3$:MeOH: aq. $NH_4OH$ afforded the product as a white solid (0.11 g, 53%) MS (ES) m/e 319 (M+H)$^+$.

To a solution of the above aminoalcohol (0.10 g, 0.31 mmol) in $CHCl_3$ (5 mL) at 0° C. was added triethylamine (0.17 g, 1.24 mmol) followed by 3-Oxo-3,4-dihydro-2H-benzo[1,4]thiazine-6-sulfonyl chloride (RM49215-119A1, 0.80 g, 0.31 mmol). After being stirred for 1 hour at 0° C., the reaction mixture was diluted with chloroform and the organic phase was washed with saturated aqueous $NaHCO_3$ solution, dried ($MgSO_4$), filtered and concentrated. Flash chromatography on silica gel using a gradient of 2-10% MeOH/$CHCl_3$ afforded the product as a white solid (45 mg, 26%) $^1H$ NMR (400 MHz, DMSO): δ10.9 (s, 1H); 8.89 (d, J=4.6 Hz, 1H); 8.39 (d, J=9.1 Hz, 1H); 7.77 (t, J=6.2 Hz, 1H); 7.70 (d, J=4.8 Hz, 1H); 7.59 (d, J=8.3 Hz, 1H); 7.44 (d, J=1.8 Hz, 1H); 7.37-7.42 (overlapping signals, 2H); 6.34 (dd, J=9.1, 7.6 Hz, 1H); 4.50 (t, J=9.2 Hz, 1H); 4.07 (s, 3H); 3.70-3.79 (m, 1H); 3.57-3.63 (overlapping signals, 3H); 3.39 (dd, J=14.2, 3.6 Hz, 1H); 3.11 (dd, J=14.2, 8.1 Hz, 1H); 2.68-2.81 (m, 2H). MS (ES) m/e 546 (M+H)$^+$.

Example 26

6-({(S)-2-Hydroxy-3-[(R)-5-(6-methoxy-[1,5]naphthyridin-4-yl)-2-oxo-oxazolidin-3-yl]-propylamino}-methyl)-4H-pyrido[3,2-b][1,4]thiazin-3-one To (R)-3-((S)-3-Amino-2-hydroxy-propyl)-5-(6-methoxy-[1,5]naphthyridin-4-yl)-oxazolidin-2-one (0.069 g, 0.22 mmol) in $CH_2Cl_2$ (7 mL) and MeOH (1.8 mL) was added 3-oxo-3,4-dihydro-2H-pyrido[3,2,b][1,4]thiazine-6-carbaldehyde (SB-735214, 0.043 g, 0.22 mmol) and the reaction mixture was stirred for 15 hours. Sodium borohydride (0.01 g, 0.26 mmol) was added followed by methanol (5 mL). After 1 hour, the reaction mixture was diluted with chloroform and washed with saturated aqueous $NaHCO_3$ solution, dried ($MgSO_4$), filtered and concentrated. Flash chromatography on silica gel using a gradient of 0-10% MeOH/$CHCl_3$ afforded the product as a white solid (0.082 g, 76%) $^1H$ NMR (400 MHz, $CDCl_3$): δ8.80 (d, J=4.6 Hz, 1H); 8.25 (d, J=9.1 Hz, 1H); 7.70 (d, J=4.4 Hz, 1H); 7.55 (d, J=7.6 Hz, 1H); 7.16 (d, J=9.1 Hz, 1H); 6.87 (d, J=7.9 Hz, 1H); 6.32 (dd, J=8.7, 7.2 Hz, 1H); 4.57 (t, J=9.4 Hz, 1H); 4.04 (s, 3H); 3.91 (m, 1H); 3.75-3.84 (overlapping signals, 2H); 3.63 (dd, J=9.2, 6.9 Hz, 1H); 3.47-3.50 (overlapping signals, 2H); 3.46 (s, 2H); 3.22 (dd, J=14.4, 6.8 Hz, 1H); 2.79 (dd, J=12.4, 3.6 Hz, 1H); 2.57 (dd, J=12.4, 8.3 Hz, 1H). MS (ES) m/e 497 (M+H)$^+$.

Example 27

3-Oxo-3,4-dihydro-2H-benzo[1,4]thiazine-6-sulfonic acid {(S)-2-hydroxy-3-[(R)-5-(6-methoxy-[1,5]naphthyridin-4-yl}-2-oxo-oxazolidin-3-yl]-propyl}-amide The title compound was prepared using the same procedure as 3-Oxo-3,4-dihydro-2H benzo[1,4]thiazine-6-sulfonic acid {(R)-2-hydroxy-3-[(R)-5-(6-methoxy-[1,5]naphthyridin-4-yl)-2-oxo-oxazolidin-3-yl]-propyl}-amide (GSK-203344A) except substituting C-((S)-2,2-dimethyl-[1,3]dioxolan-4-yl)-methylamine for C-((R)-2,2-dimethyl-[1,3]dioxolan-4-yl)-methylamine. $^1$H NMR (400 MHz, CDCl$_3$): δ8.72 (d, J=4.5 Hz, 1H); 8.19 (d, J=9.1 Hz, 1H); 7.59 (d, J=4.6 Hz, 1H); 7.35-7.42 (overlapping signals (3H); 7.11 (d, J=9.1 Hz, 1H); 6.30 (m, 1H); 4.54 (t, J=9.4 Hz, 1H); 4.01-4.08 (m, 1H); 3.99 (s, 3H); 3.58 (dd, J=8.8, 7.5 Hz, 1H); 3.49 (dd, J=14.6, 7.0 Hz, 1H); 3.44 (s, 2H); 3.27 (dd, J=14.7, 3:6 Hz, 1H); 3.08 (dd, J=13.4, 3.8 Hz, 1H); 2.99 (dd, J=13.1, 6.3 Hz, 1H); 2.62 (m, 1H). MS (ES) m/e 546 (M+H)$^+$.

Example 28

6-({(R)-2-Hydroxy-3-[(R)-5-(6-methoxy-[1,5]naphthyridin-4-yl)-2-oxo-oxazolidin-3-yl]-propylamino}-methyl)-4H-pyrido[3,2-b][1,4]thiazin-3-one The title compound was prepared using the same procedure as 6-({(S)-2-Hydroxy-3-[(R)-5-(6-methoxy-[1,5]naphthyridin-4-yl)-2-oxo-oxazolidin-3-yl]-propylamino}-methyl)-4H-pyrido[3,2-b][1,4]thiazin-3-one (GSK-207235A) except substituting C-((S)-2,2-dimethyl-[1,3]dioxolan-4-yl)-methylamine for C-((R)-2,2-dimethyl-[1,3]dioxolan-4-yl)-methylamine. $^1$H NMR (400 MHz, CDCl$_3$): 0.880 (d, J=4.5 Hz, 1H); 8.25 (d, J=9.1 Hz, 1H); 7.71 (d, J=4.6 Hz, 1H); 7.56 (d, J=7.9 Hz, 1H); 7.16 (d, J=9.1, 1H); 6.88 (d, J=7.9 Hz, 1H); 6.33 (dd, J=8.9, 7.6 Hz, 1H); 4.53 (t, J=9.4, 1H); 4.04 (s, 3H); 3.87 (m, 1H); 3.75-3.82 (overlapping signals, 2H); 3.65 (dd, J=9.2, 7.2 Hz, 1H); 3.46 (s, 2H); 3.41 (dd, J=14.4, 4.1 Hz, 1H); 3.33 (dd, J=14.5, 6.7 Hz, 1H); 2.77 (dd, J=12.2, 3.4 Hz, 1H); 2.62 (dd, J=12.4, 8.3 Hz, 1H). MS (ES) m/e 497 (M+H)$^+$.

What is claimed is:

1. A compound of formula (I)

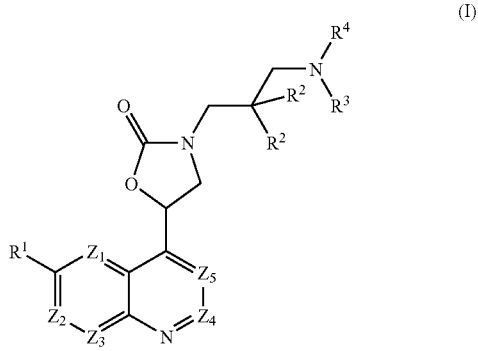

(I)

wherein:
one of $Z_1$, $Z_2$, $Z_3$, $Z_4$ and $Z_5$ is N, one is $CR^{1a}$ and the remainder are CH, or
one or two of $Z_1$, $Z_2$, $Z_3$, $Z_4$ and $Z_5$ are independently $CR^{1a}$ and the remainder are CH;

$R^1$ and $R^{1a}$ are independently hydrogen; hydroxy; ($C_{1-6}$) alkoxy unsubstituted or substituted by ($C_{1-6}$)alkoxy, amino, piperidyl, guanidino or amidino any of which is optionally N-substituted by one or two ($C_{1-6}$)alkyl, acyl or ($C_{1-6}$)alkylsulphonyl groups, CONH$_2$, hydroxy, ($C_{1-6}$) alkylthio, heterocyclylthio, heterocyclyloxy, arylthio, aryloxy, acylthio, acyloxy or ($C_{1-6}$)alkylsulphonyloxy; ($C_{1-6}$)alkoxy-substituted($C_{1-6}$)alkyl; halogen; ($C_{1-6}$)alkyl; ($C_{1-6}$)alkylthio; trifluoromethyl; trifluoromethoxy; nitro; cyano; azido; acyl; acyloxy; acylthio; ($C_{1-6}$)alkylsulphonyl; ($C_{1-6}$)alkylsulphoxide; arylsulphonyl; arylsulphoxide or an amino, piperidyl, guanidino or amidino group optionally N-substituted by one or two ($C_{1-6}$)alkyl, acyl or ($C_{1-6}$)alkylsulphonyl groups; provided that when $Z_1$, $Z_2$, $Z_3$, $Z_4$ and $Z_5$ are $CR^{1a}$ or CH, then $R^1$ is not hydrogen;

each $R^2$ is independently hydrogen, OH, NH$_2$, substituted or unsubstituted ($C_{1-6}$)alkyl, or substituted or unsubstituted ($C_{1-6}$)alkoxy;

$R^3$ is H, or substituted or unsubstituted ($C_{1-6}$)alkyl;

$R^4$ is a group -U-R$^5$ where
U is selected from CH$_2$, C=O, and SO$_2$ and
$R^5$ is a substituted or unsubstituted aryl group, or a substituted or unsubstituted bicyclic carbocyclic or heterocyclic ring system (A):

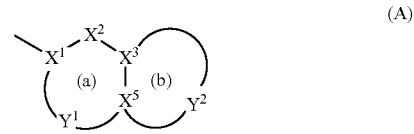

(A)

containing up to four heteroatoms in each ring in which ring (a) is aromatic and ring (b) is non-aromatic;
$X^1$ is C;
$X^2$ is N or $CR^6$;
$X^3$ and $X^5$ are C;
$Y^1$ is a 0 to 3 atom linker group, each atom of which is independently selected from N and $CR^6$;
$Y^2$ is a 2 to 6 atom linker group, each atom of $Y^2$ being independently selected from N, NR$^8$, O, S(O)$_x$, CO, $CR^6$ and $CR^6R^7$;
each of $R^6$ and $R^7$ is independently selected from: hydrogen; ($C_{1-4}$)alkylthio; halo; carboxy($C_{1-4}$)alkyl; halo($C_{1-4}$) alkoxy; halo($C_{1-4}$)alkyl; ($C_{1-4}$)alkyl; ($C_{1-4}$) alkoxycarbonyl; formyl; ($C_{1-4}$)alkylcarbonyl; ($C_{2-4}$)alkenyloxycarbonyl; ($C_{2-4}$)alkenylcarbonyl; ($C_{1-4}$)alkylcarbonyloxy; ($C_{1-4}$)alkoxycarbonyl($C_{1-4}$)alkyl; hydroxy; hydroxy($C_{1-4}$)alkyl; mercapto($C_{1-4}$)alkyl; ($C_{1-4}$)alkoxy; nitro; cyano; carboxy; amino wherein the amino group is optionally substituted by ($C_{1-4}$)alkoxycarbonyl, ($C_{1-4}$)alkylcarbonyl, ($C_{2-4}$)alkenyloxycarbonyl, ($C_{2-4}$)alkenylcarbonyl, ($C_{1-4}$)alkyl or ($C_{2-4}$)alkenyl and optionally further substituted by ($C_{1-4}$)alkyl or ($C_{2-4}$) alkenyl; ($C_{2-6}$)alkenyl; ($C_{1-4}$)alkylsulphonyl; ($C_{2-4}$) alkenylsulphonyl; or aminosulphonyl wherein the amino group is optionally mono- or di-substituted by ($C_{1-4}$)alkyl or ($C_{2-4}$)alkenyl; aryl; aryl($C_{1-4}$)alkyl; and aryl($C_{1-4}$)alkoxy;

each $R^8$ is independently hydrogen; trifluoromethyl; ($C_{1-4}$) alkyl unsubstituted or substituted by hydroxy, ($C_{1-6}$) alkoxy, ($C_{1-6}$)alkylthio, halo or trifluoromethyl; ($C_{2-4}$) alkenyl; aryl; aryl ($C_{1-4}$)alkyl; arylcarbonyl; heteroarylcarbonyl; ($C_{1-4}$)alkoxycarbonyl; ($C_{1-4}$)alkylcarbonyl; formyl; ($C_{1-6}$)alkylsulphonyl; or aminocarbonyl wherein the amino group is optionally substituted by $(C_{1-4})$alkoxycarbonyl, $(C_{1-4})$alkylcarbonyl, $(C_{2-4})$alkenyloxycarbonyl, $(C_{2-4})$alkenylcarbonyl, $(C_{1-4})$alkyl or $(C_{2-4})$alkenyl and optionally further substituted by $(C_{1-4})$ alkyl or $(C_{2-4})$alkenyl; and x is 0, 1, or 2; or a pharmaceutically acceptable salt thereof.

2. A compound according to claim 1 wherein $Z_5$ is CH or N, $Z_3$ is CH or CF and $Z_1$, $Z_2$ and $Z_4$ are each CH, or $Z_1$ is N, $Z_3$ is CH or CF and $Z_2$, $Z_4$ and $Z_5$ are each CH.

3. A compound according to claim 1 wherein $R^1$ is methoxy and $R^{1a}$ is H or when $Z_3$ is $CR^{1a}$ it may be C—F.

4. A compound according to claim 1 wherein in the heterocyclic ring (A) $Y^2$ has 3-5 atoms including $NR^8$, O or S bonded to $X^5$ and NHCO bonded via N to $X^3$, or O or NH bonded to $X^3$.

5. A compound according to claim 1 wherein $R^6$ and $R^7$ are independently hydrogen; hydroxy; halo; or $(C_{1-4})$alkyl substituted or unsubstituted by hydroxy, $(C_{1-6})$alkoxy, $(C_{1-6})$alkylthio, halo or trifluoromethyl; $(C_{2-4})$alkenyl; $(C_{1-4})$alkoxycarbonyl.

6. A compound according to claim 1 wherein $R^5$ is selected from 1H-Indol-2-yl, quinolin-8-ol-2-yl, 3-Oxo-3,4-dihydro-2H-benzo[1,4]oxazine-6-yl, 4H-benzo[1,4]oxazin-3-one-6-yl, 4-fluoro-1H-benzoimidazol-2-yl, 3,6-dimethyl-3H-benzooxazol-2-one, 4H-benzo[1,4]thiazin-3-one-6-yl, 3-Oxo-3,4-dihydro-2H-benzo[1,4]thiazine-6-yl, 4-Oxo-2,3,4,5-tetrahydro-benzo[b][1,4]thiazepine-7-yl, 7-Chloro-3-oxo-3,4-dihydro-2H-benzo[1,4]thiazine-6-yl, 3-oxo-3,4-dihydro-2H-pyrido[3,2-b][1,4]oxazine-6-yl, and 4H-pyrido[3,2-b][1,4]oxazin-3-one-6-yl.

7. A compound according to claim 1 which is selected from:
  3-Oxo-3,4-dihydro-2H-benzo[1,4]thiazine-6-sulfonic acid {3-[(R)-5-(6-methoxy-quinolin-4-yl)-2-oxo-oxazolidin-3-yl]-propyl}-amide;
  4-Oxo-2,3,4,5-tetrahydro-benzo[b][1,4]thiazepine-7-sulfonic acid {3-[(R)-5-(6-methoxy-quinolin-4-yl)-2-oxo-oxazolidin-3-yl]-propyl}-amide;
  3-Oxo-3,4-dihydro-2H-benzo[1,4]oxazine-6-sulfonic acid {3-[(R)-5-(6-methoxy-quinolin-4-yl)-2-oxo-oxazolidin-3-yl]-propyl}-amide;
  7-Chloro-3-oxo-3,4-dihydro-2H-benzo[1,4]thiazine-6-sulfonic acid {3-[(R)-5-(6-methoxy-quinolin-4-yl)-2-oxo-oxazolidin-3-yl]-propyl}-amide; and
  3-Oxo-3,4-dihydro-2H-benzo[1,4]thiazine-6-sulfonic acid {3-[(R)-5-(8-fluoro-6-methoxy-quinolin-4-yl)-2-oxo-oxazolidin-3-yl]-propyl}-amide; or
a pharmaceutically acceptable salt thereof.

8. A pharmaceutical composition comprising a compound according to claim 1 and a pharmaceutically acceptable carrier.

9. A method of treating bacterial infections due to an organism selected from *Staphylococcus aureus, Staphylococcus epidermis, Streptococcus pneumoniae, Streptococcus pyogenes, Enterococcus faecalis, Enterococcus faecium, Haemophilus influenzae, E. coli,* and *Moraxella catarrhalis,* in mammals which comprises the administration to a mammal in need thereof an effective amount of a compound according to claim 1.

10. A pharmaceutical composition comprising a compound according to claim 7 and a pharmaceutically acceptable carrier.

11. A method of treating bacterial infections in mammals due to an organism selected from *Staphylococcus aureus, Staphylococcus epidermis, Streptococcus pneumoniae, Streptococcus pyogenes, Enterococcus faecalis, Enterococcus faecium, Haemophilus influenzae, E. coli,* and *Moraxella catarrhalis* which comprises the administration to a mammal in need thereof an effective amount of a compound according to claim 7.

12. A compound according to claim 1 which is: 3-Oxo-3,4-dihydro-2H-pyrido[3,2-b][1,4]thiazine-6-carboxylic acid {3-[(R)-5-(6-methoxy-quinolin-4-yl)-2-oxo-oxazolidin-3-yl]-propyl}-amide; or a pharmaceutically acceptable salt thereof.

13. A compound according to claim 1 which is selected from:
  6-({3-[(R)-5-(6-Methoxy-quinolin-4-yl)-2-oxo-oxazolidin-3-yl]-propyl}amino)-methyl-4H-benzo[1,4]oxazin-3-one;
  6-({3-[(R)-5-(6-Methoxy-quinolin-4-yl)-2-oxo-oxazolidin-3-yl]-propyl}amino)-methyl-4H-benzo[1,4]thiazin-3-one;
  6-({3-[(R)-5-(6-Methoxy-quinolin-4-yl)-2-oxo-oxazolidin-3-yl]-propylamino}-methyl)-4H-pyrido[3,2-b][1,4]oxazin-3-one; and
  6-({3-[(R)-5-(8-Fluoro-6-methoxy-quinolin-4-yl)-2-oxo-oxazolidin-3-yl]-propylamino}-methyl)-4H-pyrido[3,2-b][1,4]oxazin-3-one; or
a pharmaceutically acceptable salt thereof.

14. A compound according to claim 1 selected from:
  3-Oxo-3,4-dihydro-2H-benzo[1,4]thiazine-6-sulfonic acid {3-[(R)-5-(6-methoxy-[1,5]naphthyridin-4-yl)-2-oxo-oxazolidin-3-yl]-propyl}-amide;
  3-Oxo-3,4-dihydro-2H-benzo[1,4]thiazine-6-sulfonic acid {3-[(S)-5-(6-methoxy-[1,5]naphthyridin-4-yl)-2-oxo-oxazolidin-3-yl]-propyl}-amide;
  3-Oxo-3,4-dihydro-2H-benzo[1,4]oxazine-6-sulfonic acid {3-[(R)-5-(6-methoxy-[1,5]naphthyridin-4-yl)-2-oxo-oxazolidin-3-yl]-propyl}-amide;
  3-Oxo-3,4-dihydro-2H-benzo[1,4]thiazine-6-sulfonic acid {3-[(R)-5-(6-methoxy-[1,5]naphthyridin-4-yl)-2-oxo-oxazolidin-3-yl]-2,2-dimethyl-propyl}-amide;
  2,3-Dihydro-benzo[1,4]dioxine-6-sulfonic acid {3-[5-(6-methoxy-[1,5]naphthyridin-4-yl)-2-oxo-oxazolidin-3-yl]-propyl}-amide;
  3-Oxo-3,4-dihydro-2H-benzo[1,4]thiazine-6-sulfonic acid {(R)-2-hydroxy-3-[(R)-5-(6-methoxy-[1,5]naphthyridin-4-yl)-2-oxo-oxazolidin-3-yl]-propyl}-amide; and
  3-Oxo-3,4-dihydro-2H-benzo[1,4]thiazine-6-sulfonic acid {(S)-2-hydroxy-3-[(R)-5-(6-methoxy-[1,5]naphthyridin-4-yl}-2-oxo-oxazolidin-3-yl]-propyl}-amide; or
a pharmaceutically acceptable salt thereof.

15. A compound according to claim 1 selected from:
  6-({3-[5-(6-Methoxy-[1,5]naphthyridin-4-yl)-2-oxo-oxazolidin-3-yl]-propylamino}-methyl)-4H-pyrido[3,2-b][1,4]thiazin-3-one;
  6-({3-[5-(6-Methoxy-[1,5]naphthyridin-4-yl)-2-oxo-oxazolidin-3-yl]-propylamino}-methyl)-4H-pyrido[3,2-b][1,4]oxazin-3-one;
  6-({(S)-2-Hydroxy-3-[(R)-5-(6-methoxy-[1,5]naphthyridin-4-yl)-2-oxo- oxazolidin-3-yl]-propylamino}-methyl)-4H-pyrido[3,2-b][1,4]thiazin-3-one; and
  6-({(R)-2-Hydroxy-3-[(R)-5-(6-methoxy-[1,5]naphthyridin-4-yl)-2-oxo-oxazolidin-3-yl]-propylamino}-methyl)-4H-pyrido[3,2-b][1,4]thiazin-3-one; or a pharmaceutically acceptable salt thereof.

16. A pharmaceutical composition comprising a compound according to claim 12 and a pharmaceutically acceptable carrier.

17. A pharmaceutical composition comprising a compound according to claim 13 and a pharmaceutically acceptable carrier.

18. A pharmaceutical composition comprising a compound according to claim 14 and a pharmaceutically acceptable carrier.

19. A pharmaceutical composition comprising a compound according to claim 15 and a pharmaceutically acceptable carrier.

20. A method of treating bacterial infections due to an organism selected from *Staphylococcus aureus, Staphylococcus epidermidis, Streptococcus pneumoniae, Streptococcus pyogenes, Enterococcus faecalis, Enterococcus faecium, Haemophilus influenzae, E. coli,* and *Moraxella catarrhalis* in mammals which comprises the administration to a mammal in need thereof an effective amount of a compound according to claim 12.

21. A method of treating bacterial infections due to an organism selected from *Staphylococcus aureus, Staphylococcus epidermidis, Streptococcus pneumoniae, Streptococcus pyogenes, Enterococcus faecalis, Enterococcus faecium, Haemophilus influenzae, E. coli,* and *Moraxella catarrhalis* in mammals which comprises the administration to a mammal in need thereof an effective amount of a compound according to claim 13.

22. A method of treating bacterial infections due to an organism selected from *Staphylococcus aureus, Staphylococcus epidermidis, Streptococcus pneumoniae, Streptococcus pyogenes, Enterococcus faecalis, Enterococcus faecium, Haemophilus influenzae, E. coli,* and *Moraxella catarrhalis* in mammals which comprises the administration to a mammal in need thereof an effective amount of a compound according to claim 14.

23. A method of treating bacterial infections due to an organism selected from *Staphylococcus aureus, Staphylococcus epidermidis, Streptococcus pneumoniae, Streptococcus pyogenes, Enterococcus faecalis, Enterococcus faecium, Haemophilus influenzae, E. coli,* and *Moraxella catarrhalis* in mammals which comprises the administration to a mammal in need thereof an effective amount of a compound according to claim 15.

* * * * *